(12) United States Patent
Pingali et al.

(10) Patent No.: US 8,785,463 B2
(45) Date of Patent: Jul. 22, 2014

(54) GPR 119 AGONISTS

(75) Inventors: Harikishore Pingali, Ahmedabad (IN); Pandurang Zaware, Ahmedabad (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

(21) Appl. No.: 13/824,552

(22) PCT Filed: Oct. 5, 2011

(86) PCT No.: PCT/IN2011/000694
§ 371 (c)(1), (2), (4) Date: Jun. 3, 2013

(87) PCT Pub. No.: WO2012/046249
PCT Pub. Date: Apr. 12, 2012

(65) Prior Publication Data
US 2013/0252980 A1    Sep. 26, 2013

(30) Foreign Application Priority Data
Oct. 8, 2010    (IN) .......................... 2803/MUM/2010

(51) Int. Cl.
*A01N 43/54*    (2006.01)
*A61K 31/505*   (2006.01)
*A61K 31/506*   (2006.01)
*C07D 239/52*   (2006.01)

(52) U.S. Cl.
CPC ............ *A61K 31/506* (2013.01); *C07D 239/52* (2013.01)
USPC ......................................... 514/269; 544/319

(58) Field of Classification Search
CPC ............................. C07D 239/52; A61K 31/506
USPC ........................................ 544/319; 514/269
See application file for complete search history.

(56) References Cited

FOREIGN PATENT DOCUMENTS

| EP | 2 210 886 | 7/2010 |
|----|-----------|--------|
| WO | WO 2007/017095 | 2/2007 |
| WO | WO 2007/035355 | 3/2007 |
| WO | WO 2009046416 | * 4/2009 |

OTHER PUBLICATIONS

T. Overton et al., 153 British Journal of Pharmacology, 576-581 (2008).*
Z-L Chu et al., 24 Molecular Endocrinology, 161-170 (2010).*
International Search Report for PCT/IN2011/000694, mailed Mar. 6, 2012.
International Preliminary Report on Patentability for PCT/IN2011/000694, dated Jan. 21, 2013.
Jones, R.M. et al., The Emergence of GPR119 Agonists as Anti-Diabetic Agents >>, Annual Reports in Medicinal Chemistry, vol. 44, (Jan. 1, 2009), pp. 149-170.

* cited by examiner

*Primary Examiner* — Deepak Rao
*Assistant Examiner* — Alexander R Pagano
(74) *Attorney, Agent, or Firm* — Nixon & Vanderhye P.C.

(57) ABSTRACT

The present invention relates to novel GPR 119 agonists of the general formula (I), their tautomeric forms, their stereoisomers, their pharmaceutically acceptable salts, pharmaceutical compositions containing them, methods for their preparation, use of these compounds in medicine and the intermediates involved in their preparation.

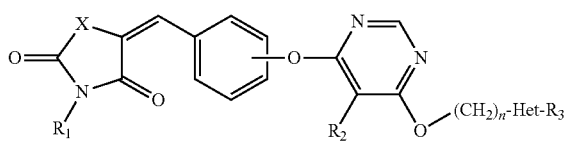

12 Claims, No Drawings

GPR 119 AGONISTS

This application is the U.S. national phase of International Application No. PCT/IN2011/000694, filed 5 Oct. 2011, which designated the U.S. and claims priority to India Application No. 2803/MUM/2010, filed 8 Oct. 2010, the entire contents of each of which are hereby incorporated by reference.

FIELD OF INVENTION

The present invention relates to novel GPR 119 agonists of the general formula (I), their tautomeric forms, their stereoisomers, their pharmaceutically acceptable salts, pharmaceutical compositions containing them, methods for their preparation, use of these compounds in medicine and the intermediates involved in their preparation.

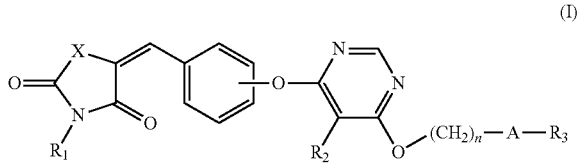

(I)

The present invention is directed to G-protein coupled receptor (GPCR) agonists that are useful for the treatment of obesity, diabetes and related metabolic disorders.

The compounds of the general formula (I) lower blood glucose, regulate peripheral satiety, lower or modulate triglyceride levels and/or cholesterol levels and/or low-density lipoproteins (LDL) and raises the high-density lipoproteins (HDL) plasma levels and hence are useful in combating different medical conditions, where such lowering (and raising) is beneficial. Thus, it could be used in the treatment and/or prophylaxis of obesity, hyperlipidaemia, hypercholesteremia, hypertension, atherosclerotic disease events, vascular restenosis, diabetes and many other related conditions.

The compounds of general formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders.

These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such as cardiovascular diseases, like arteriosclerosis, atherosclerosis; diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

BACKGROUND OF THE INVENTION

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either don't produce insulin or can't efficiently use the insulin they produce; therefore, they can't move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

About 5% to 10% of the people who have diabetes have IDDM. These individuals don't produce insulin and therefore must inject insulin to keep their blood glucose levels normal. IDDM is characterized by low or undetectable levels of endogenous insulin production caused by destruction of the insulin-producing β cells of the pancreas, the characteristic that most readily distinguishes IDDM from NIDDM. IDDM, once termed juvenile-onset diabetes, strikes young and older adults alike.

Approximately 90 to 95% of people with diabetes have Type II (or NIDDM). NIDDM subjects produce insulin, but the cells in their bodies are insulin resistant: the cells don't respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NIDDM; many NIDDM patients have normal or even elevated blood insulin levels, while other NIDDM patients have inadequate insulin production (Rotwein, R. et al. N. Engl. J. Med. 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically non-apparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. Emery and Rimoin's Principles and Practice of Medical Genetics 3$^{rd}$ Ed. 1:1401-1402 (1996)).

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity and diabetes are among the most common human health problems in industrialized societies. In industrialized countries a third of the population is at least 20% overweight. In the United States, the percentage of obese people has increased from 25% at the end of the 1970s, to 33% at the beginning the 1990s. Obesity is one of the most important risk factors for NIDDM. Definitions of obesity differ, but in general, a subject weighing at least 20% more than the recommended weight for his/her height and build is considered obese. The risk of developing NIDDM is tripled in subjects 30% overweight, and three-quarters with NIDDM are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increase insulin secretion balances insulin resistance and protects patients from hyperglycemia (Le Stunff, et al. Diabetes 43, 696-702 (1989)). However, after several decades, β cell function deteriorates and non-insulin-dependent diabetes develops in about 20% of the obese population (Pederson, P. Diab. Metab. Rev. 5, 505-509 (1989)) and (Brancati, F. L., et al., Arch. Intern. Med. 159, 957-963 (1999)). Given its high prevalence in modern societies, obesity has thus become the leading risk factor for NIDDM (Hill, J. O., et al., Science 280, 1371-1374 (1998)). The present invention is directed to G-protein coupled receptor (GPCR) agonists. In particular, the present invention is directed to agonists of GPR 119 that are useful for the treatment of obesity, e.g. as regulators of satiety, and for the treatment of diabetes.

Obesity is characterized by an excessive adipose tissue mass relative to body size. Clinically, body fat mass is estimated by the body mass index (BMI; weight(kg)/height(m)$^2$), or waist circumference. Individuals are considered obese when the BMI is greater than 30 and there are established medical consequences of being overweight. It has been an accepted medical view for some time that an increased body weight, especially as a result of abdominal body fat, is associated with an increased risk for diabetes, hypertension, heart disease, and numerous other health complications, such as arthritis, stroke, gallbladder disease, muscular and respiratory problems, back pain and even certain cancers. However, the factors which predispose a fraction of patients to alteration of insulin secretion in response to fat accumulation remain unknown.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centres are also able to sense peripheral hormones involved in the maintenance of body weight and degree of adiposity, such as insulin and leptin, and fat tissue derived peptides.

Drugs aimed at the pathophysiology associated with insulin dependent Type I diabetes and non-insulin dependent Type II diabetes have many potential side effects and do not adequately address the dyslipidaemia and hyperglycaemia in a high proportion of patients. Treatment is often focused at individual patient needs using diet, exercise, hypoglycaemic agents and insulin, but there is a continuing need for novel antidiabetic agents, particularly ones that may be better tolerated with fewer adverse effects.

Similarly, metabolic syndrome (syndrome X) which is characterized by hypertension and its associated pathologies including atherosclerosis, lipidemia, hyperlipidemia and hypercholesterolemia have been associated with decreased insulin sensitivity which can lead to abnormal blood sugar levels when challenged. Myocardial ischemia and microvascular disease is an established morbidity associated with untreated or poorly controlled metabolic syndrome.

There is a continuing need for novel antiobesity and antidiabetic agents, particularly ones that are well tolerated with few adverse effects.

The present invention is directed to G-protein coupled receptor agonists of GPR 119 that are useful for the treatment of obesity, e.g. as regulators of satiety, and for the treatment of diabetes. GPR 119 is a GPCR identified as SNORF25 in WO00/50562 which discloses both the human and rat receptors, U.S. Pat. No. 6,468,756 also discloses the mouse receptor (accession numbers: AAN95194 (human), AAN95195 (rat) and ANN95196 (mouse)).

In humans, GPR 119 is expressed in the pancreas, small intestine, colon and adipose tissue. A Role of G Protein-Coupled Receptor 119 expressed in ☐Cell-in glycemic control by enhancing glucose dependent insulin release was demonstrated by using an agonist of GPR-119 (Endocrinology 148(6):2601-2609). Further the anti obesity effects of GPR-119 agonist which suppress food intake in rats and reduce body weight gain and white adipose tissue deposition upon subchronic oral administration to high-fat-fed rats was also demonstrated (Cell Metabolism 3, 167-175). GPR119 therefore represents a novel and attractive potential target for the therapy of obesity and related metabolic disorders.

International patent applications WO2005/061489, WO2007116230, WO2007116229, WO2007003964, WO2007003962, WO2007003961, and WO2006070208, WO2008076243, WO2008083238, WO2009106561, WO2009012275, WO2009141238, WO2009150144, WO2010009183, WO2010084512, WO2010006191, WO2010048149 discloses heterocyclic derivatives as GPR 119 receptor agonists. However, the therapeutic potential of these compounds to treat diseases has not yet been proved and so there remains the need to develop newer medicines which are better or of comparable efficacy with the present treatment regimes, have lesser side effects and require a lower dosage regime We herein disclose novel compounds of formula (I) useful as antidiabetic, anti-obesity, hypolipidaemic, hypolipoproteinemic, and antihyperglycemic agents which may have additional body weight lowering effect and beneficial effect in the treatment and/or prophylaxis of diseases caused by hyperlipidaemia, diseases classified under Syndrome X and atherosclerosis, and methods for their preparation.

PREFERRED EMBODIMENTS OF THE INVENTION

The main objective of the present invention is to provide novel GPR 119 agonists represented by the general formula (I), their tautomeric forms, their stereoisomers, their pharmaceutically acceptable salts, and pharmaceutical compositions containing them or their mixtures thereof.

In an embodiment of the present invention is provided a process for the preparation of compounds represented by the general formula (I), their tautomeric forms, their stereoisomers, their pharmaceutically acceptable salts.

In a further embodiment of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

DETAILED DESCRIPTION OF THE INVENTION

Accordingly, the present invention relates to compounds of the general formula (I)

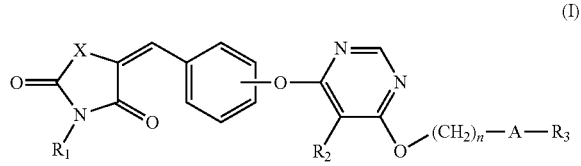

their tautomeric forms, their stereoisomers, their pharmaceutically acceptable salts, and pharmaceutical compositions containing them wherein "$R_1$" represents H, optionally substituted groups selected from linear or branched ($C_1$-$C_6$), alkyl, haloalkyl, ($C_1$-$C_6$) alkenyl, cycloalkyl, cycloalkylalkyl, heterocyclyl, heterocyclylalkyl, aryl, aralkyl, heteroaryl, heteroarylalkyl, alkylsulfonyl, arylsulfonyl, or the groups represented by $(CH_2)_m CO_2R_4$, $(CH_2)_m COR_4$ or $(CH_2)_m CONH_2$ wherein $R_4$ at each occurrence independently represents H, groups selected from linear or branched ($C_1$-$C_6$)alkyl, cycloalkyl, aryl, heterocyclyl or heteroaryl and m=0 to 3;

"$R_2$" represents H, cyano, nitro, formyl, linear or branched ($C_1$-$C_6$)alkyl, ($C_1$-$C_6$)alkoxy groups;

"$R_3$" represents optionally substituted groups selected from linear or branched ($C_1$-$C_6$)alkyl, aryl, aralkyl, cycloalkyl, cycloalkylalkyl, heterocyclyl, hererocyclylalkyl, heteroaryl, heteroaralkyl or the groups represented by $C(O)OR_5$, $C(O)R_5$, and $SO_2R_5$ wherein $R_5$ at each occurrence independently represents H or optionally substituted groups selected from linear or branched ($C_1$-$C_6$)alkyl, aryl, aralkyl, cycloalkyl, cycloalkylalkyl, heterocyclyl, hererocyclylalkyl, heteroaryl, heteroaralkyl groups;

"n" represents an integer from 0 to 3;

"A" represents

wherein "p" represents integers from 1 to 3;

"X" represents O, S;

In a preferred embodiment, $R_1$ is selected from linear or branched ($C_1$-$C_6$)alkyl, haloalkyl; ($C_1$-$C_6$)alkenyl, cycloalkyl, aralkyl alkylsulfonyl, arylsulfonyl, the groups represented by $(CH_2)_m CO_2R_4$, $(CH_2)_m COR_4$ or $(CH_2)_m CONH_2$ wherein $R_4$ at each occurrence independently represents H, groups selected from linear or branched ($C_1$-$C_6$) alkyl, cycloalkyl, aryl, heterocyclyl or heteroaryl and m=0 to 3;

In another preferred embodiment, $R_2$ is selected from H, nitro, linear or branched ($C_1$-$C_6$)alkyl, ($C_1$-$C_6$)alkoxy groups;

In a still preferred embodiment are described compounds of formula (I) wherein $R_1$ is selected from linear or branched ($C_1$-$C_6$)alkyl, haloalkyl, ($C_1$-$C_6$) alkenyl, aralkyl alkylsulfonyl, arylsulfonyl the groups represented by $(CH_2)_m CO_2R_4$, $(CH_2)_m COR_4$ or $(CH_2)_m CONH_2$ wherein $R_4$ at each occurrence independently represents groups selected from linear or branched ($C_1$-$C_6$) alkyl, aryl, m=0 to 3;

In a still preferred embodiment are described compounds of formula (I) wherein $R_2$ is selected from H, linear or branched ($C_1$-$C_6$) alkyl.

In an embodiment, when any of '$R_1$', '$R_3$', $R_4$' or '$R_5$' is substituted with one or many groups, as applicable, the substituents may be independently selected from the groups comprising hydroxyl, oxo, halo, thio, nitro, amino, cyano, formyl, or substituted or unsubstituted groups selected from amidino, alkyl, haloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkylsulfonyloxy, alkoxycarbonylamino, aryloxycarbonylamino, aralkyloxycarbonylamino, aminocarbonylamino, alkylaminocarbonylamino, alkoxyamino, hydroxylamino, sulfenyl derivatives, sulfonyl derivatives, sulfonic acid and its derivatives.

When the substituents on any of '$R_1$', '$R_3$', $R_4$' or '$R_5$' are further substituted, those substituents may be independently selected from hydroxyl, oxo, halo, thio, nitro, amino, cyano, formyl, or substituted or unsubstituted groups selected from amidino, alkyl, haloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkylsulfonyloxy, alkoxycarbonylamino, aryloxycarbonylamino, aralkyloxycarbonylamino, aminocarbonylamino, alkylaminocarbonylamino, alkoxyamino, hydroxylamino, sulfenyl derivatives, sulfonyl derivatives, sulfonic acid and its derivatives.

The various groups, radicals and substituents used anywhere in the specification are further described in the following paragraphs.

the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;

the "alkenyl" group used either alone or in combination with other radicals, is selected from a radical containing from two to six carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl and the like; the "alkenyl" group includes dienes and trienes of straight and branched chains;

the "alkynyl" group used either alone or in combination with other radicals, is selected from a linear or branched radical containing two to six carbon atoms, more preferably thienyl, 1-propynyl, 2-propynyl, 1-butynyl, 2-butynyl, 3-butynyl, 1-pentynyl, 2-pentynyl, 3-pentynyl, 4-pentynyl, 1-hexynyl, and the like. The term "alkynyl" includes di- and tri-ynes;

the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like; The terms "bicycloalkyl" means more than one cycloalkyl groups fused together;

the "cycloalkenyl" group used either alone or in combination with other radicals, are preferably selected from cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl and the like;

"Aryl" means a mono- or polycyclic aromatic ring system containing carbon ring atoms. The preferred aryls are monocyclic or bicyclic 6-10 membered aromatic ring systems. Phenyl and naphthyl are preferred aryls.

"Heterocycle" or "heterocyclyl" refers to saturated or unsaturated non-aromatic rings or ring systems containing at least one heteroatom selected from O, S, N further including the oxidized forms of sulfur, namely SO & $SO_2$ & suitable alkyl groups defined elsewhere in the specification linked to the heterocyclic moiety. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, dihydropyran, oxathiolane, dithiolane, 1,3-dioxane, 1,3-dithiane, oxathiane, thiomorpholine etc.

"Heteroaryl" means mono or polycyclic aromatic or partially aromatic heterocycle that contains at least one ring heteroatom selected from O, S and N. Heteroaryls thus include heteroaryls fused to the other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, to pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl etc. For heterocyclyl and heteroaryl groups, rings and ring systems containing from 3-15 carbon atoms are included, forming 1-3 rings.

the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;

the "cycloalkoxy" group used either alone or in combination with other radicals, is selected from groups containing an cycloalkyl radical, as defined above, attached directly to an oxygen atom, more preferably groups selected from cyclopropoxy, cyclobutoxy, cyclopentyloxy, cyclohexyloxy, cycloheptyloxy and the like;

the "aryloxy" group used either alone or in combination with other radicals, is selected from groups containing an aryl radical, as defined above, attached directly to an oxygen atom, more preferably groups selected from phenoxy, naphthyloxy, tetrahydronaphthyloxy, biphenyloxy, and the like;

the "aralkyl" group used either alone or in combination with other radicals, is selected from groups containing an aryl radical, as defined above, attached directly to an alkyl radical, as define above, more preferably groups selected from benzyl, phenethyl, and the like;

the "aralkoxy" group used either alone or in combination with other radicals, is selected from groups containing an aralkyl radical, as defined above, attached directly to an oxygen atom, more preferably groups selected from benzyloxy, phenethyloxy, and the like;

the "heteroaralkyl" group used either alone or in combination with other radicals, is selected from groups containing an heteroaryl radical, as defined above, attached directly to an alkyl radicals, as define above, more preferably groups selected from pyridinealkyl, thiophenealkyl, quinolinealkyl, and the like;

the "alkenoxy" group used either alone or in combination with other radicals, is selected from groups containing an alkenyl radical, as defined above, attached to an oxygen atom, more preferably selected from vinyloxy, allyloxy, butenoxy, pentenoxy, hexenoxy, and the like;

the "haloalkyl" group is selected from an alkyl radical, as defined above, suitably substituted with one or more halogens; such as perhaloalkyl, more preferably, perfluoro($C_1$-$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "haloalkoxy" group is selected from suitable haloalkyl, as defined above, directly attached to an oxygen atom, more preferably groups selected from fluoromethoxy, chloromethoxy, fluoroethoxy, chloroethoxy and the like;

the "perhaloalkoxy" group is selected from a suitable perhaloalkyl radical, as defined above, directly attached to an oxygen atom, more preferably groups selected from trifluoromethoxy, trifluoroethoxy, and the like;

the groups "heteroaryloxy", "heteroaralkoxy", "heterocycloxy", "heterocylylalkoxy" are selected from suitable heteroaryl, heteroarylalkyl, heterocyclyl, heterocylylalkyl groups respectively, as defined above, attached to an oxygen atom;

the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;

the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like;

the "acylamino" group used either alone or in combination with other radicals, is selected from a suitable acyl group as defined earlier, attached to an amino radical, more preferably such groups are selected from $CH_3CONH$, $C_2H_5CONH$, $C_3H_7CONH$, $C_4H_9CONH$, $C_6H_5CONH$ and the like, which may be substituted;

the "mono-substituted amino" group used either alone or in combination with other radicals, represents an amino group substituted with one group selected from $(C_1-C_6)$ alkyl, substituted alkyl, aryl, substituted aryl or arylalkyl groups as defined earlier, more preferably such groups are selected from methylamine, ethylamine, n-propylamine, n-butylamine, n-pentylamine and the like;

the "disubstituted amino" group used either alone or in combination with other radicals, represents an amino group, substituted with two radicals that may be same or different selected from $(C_1-C_6)$alkyl, substituted alkyl, aryl, substituted aryl, or arylalkyl groups, as defined above, more preferably the groups are selected from dimethylamino, methylethylamino, diethylamino, phenylmethyl amino and the like;

the "arylamino" used either alone or in combination with other radicals, represents an aryl group, as defined above, linked through amino having a free valence bond from the nitrogen atom, more preferably the groups are selected from phenylamino, naphthylamino, N-methyl anilino and the like;

the "oxo" or "carbonyl" group used either alone (—C=O—) or in combination with other radicals such as alkyl described above, for e.g. "alkylcarbonyl", denotes a carbonyl radical (—C=O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "amide" group used alone or in combination with other radicals, represents an aminocarbonyl radical ($H_2N$—C=O), wherein the amino group is mono- or di-substituted or unsubstituted, more preferably the groups are selected from methyl amide, dimethyl amide, ethyl amide, diethyl amide, and the like;

the "aminocarbonyl" group used either alone or in combination with other radicals, to may be selected from 'aminocarbonyl', 'aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote amiocarbonyl radicals substituted, respectively, with one aryl radical, or one alkyl, and one aryl radical. The term "aminocarbonylalkyl" includes alkyl radicals substituted with aminocarbonyl radicals;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, butylthio, pentylthio and the like or cyclic alkylthio selected from cyclopropylthio, cyclobutylthio, cyclopentylthio, cyclohexylthio and the like, which may be optionally substituted;

the "thioalkyl" group used either alone or in combination with other radicals, denotes an alkyl group, as defined above, attached to a group of formula SR', where R' represents hydrogen, alkyl or aryl group, e.g. thiomethyl, methylthiomethyl, phenylthiomethyl and the like, which may be optionally substituted.

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "aminocarbonylamino", "alkylaminocarbonylamino", "dialkylaminocarbonylamino" groups used alone or in combination with other radicals, is a carbonylamino (—CONH$_2$) group, attached to amino(NH$_2$), alkylamino group or dialkylamino group respectively, where alkyl group is as defined above;

the "amidino" group used either alone or in combination with other radicals, represents a C(=NH)—NH$_2$ radical; the "alkylamidino" group represents an alkyl radical, as described above, attached to an amidino group;

the "alkoxyamino" group used either alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above;

the "sulfenyl" group or "sulfenyl derivatives" used alone or in combination with other radicals, represents a bivalent group, —SO— or R$_x$SO, where R$_x$ is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —SO$_2$—, or R$_x$SO$_2$—, where R$_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like.

the "sulfonyloxy" group used either alone or in combination with other radicals, to with other terms such as alkylsulfonyloxy, represents a divalent radical SO$_3$—, or R$_x$SO$_3$—, where R$_x$ is as defined above. More preferably, the groups may be selected from "alkylsulfonyl" wherein suitable alkyl radicals, selected from those defined above, is attached to a sulfonyloxy radical, such as methanesulfonyloxy, ethanesulfonyloxy, propanesulfonyloxy and the like, "arylsulfonyl" wherein an aryl radical, as defined above, is attached to a sulfonyl radical, such as benzenesulfonyloxy and the like Suitable groups and substituent's on the groups may be selected from those described anywhere in the specification. Particularly useful compounds may be selected from (Z)-tert-Butyl 4-((6-4-((2,4-dioxothiazolidin-5-ylidene)methyl)phenoxy)-5-methylpyrimidin-4-yl)oxy)piperidine-1-carboxylate;

(Z)-tert-Butyl-4-((6-(4-((3-(2-ethoxy-2-oxoethyl)-2,4-dioxothiazolidin-5-ylidene)methyl)phenoxy)-5-methylpyrimidin-4-yl)oxy)piperidine-1-carboxylate;

(Z)-5-(4-((6-((1-(5-Ethylpyrimidin-2-yl)piperidin-4-yl)oxy)-5-methylpyrimidin-4-yl)oxy)benzylidene)-3-(methylsulfonyl)thiazolidine-2,4-dione;

(Z)-Ethyl-4-((5-methyl-6-(3-((3-methyl-2,4-dioxothiazolidin-5-ylidene)methyl)phenoxy)pyrimidin-4-yl)oxy)piperidine-1-carboxylate.

(Z)-5-(3-((5-Methyl-6-((1-(methylsulfonyl)piperidin-4-yl)oxy)pyrimidin-4-yl)oxy)benzylidene)thiazolidine-2,4-dione.

(Z)-5-(3-((6-((1-acetylpiperidin-4-yl)oxy)-5-methylpyrimidin-4-yl)oxy)benzylidene)thiazolidine-2,4-dione.

(Z)-5-(4-((6-((1-(3-iso-Propyl-1,2,4-oxadiazol-5-yl)piperidin-4-yl)oxy)-5-methylpyrimidin-4-yl)oxy)benzylidene)thiazolidine-2,4-dione.

(Z)-tert-Butyl 4-((6-(4-((2,4-dioxothiazolidin-5-ylidene)methyl)-2-methoxyphenoxy)-5-methylpyrimidin-4-yl)oxy)piperidine-1-carboxylate.

(Z)-tert-Butyl 4-((6-(3-((2,4-dioxothiazolidin-5-ylidene)methyl)phenoxy)-5-methylpyrimidin-4-yl)oxy)piperidine-1-carboxylate.

(Z)-5-(4-((6-((1-(3-iso-Propyl-1,2,4-oxadiazol-5-yl)piperidin-4-yl)oxy)pyrimidin-4-yl)oxy)benzylidene)thiazolidine-2,4-dione.

(Z)-Methyl 4-((6-(4-((2,4-dioxothiazolidin-5-ylidene)methyl)phenoxy)-5-methylpyrimidin-4-yl)oxy)piperidine-1-carboxylate.

(Z)-tert-Butyl 4-((6-(4-((2,4-dioxothiazolidin-5-ylidene)methyl)phenoxy)pyrimidin-4-yl)oxy)piperidine-1-carboxylate.

(Z)-Benzyl 4-((6-(4-((2,4-dioxothiazolidin-5-ylidene)methyl)phenoxy)-5-methylpyrimidin-4-yl)oxy)piperidine-1-carboxylate.

(Z)-Ethyl 4-((6-(4-((2,4-dioxothiazolidin-5-ylidene)methyl)phenoxy)-5-methylpyrimidin-4-yl)oxy)piperidine-1-carboxylate.

(Z)-iso-Butyl 4-((6-(4-((2,4-dioxothiazolidin-5-ylidene)methyl)phenoxy)-5-methylpyrimidin-4-yl)oxy)piperidine-1-carboxylate.

(Z)-iso-Propyl 4-((6-(4-((2,4-dioxothiazolidin-5-ylidene)methyl)phenoxy)-5-methylpyrimidin-4-yl)oxy)piperidine-1-carboxylate.

(Z)-5-(4-((5-Methyl-6-((1-(pyrimidin-2-yl)piperidin-4-yl)oxy)pyrimidin-4-yl)oxy)benzylidene)thiazolidine-2,4-dione.

(Z)-tert-Butyl 2-(((6-(4-((2,4-dioxothiazolidin-5-ylidene)methyl)phenoxy)-5-methylpyrimidin-4-yl)oxy)methyl)pyrrolidine-1-carboxylate.

(Z)-tert-Butyl 4-((6-(3-((2,4-dioxothiazolidin-5-ylidene)methyl)phenoxy)pyrimidin-4-yl)oxy)piperidine-1-carboxylate.

(Z)-Ethyl 4-((6-(3-((2,4-dioxothiazolidin-5-ylidene)methyl)phenoxy)-5-methylpyrimidin-4-yl)oxy)piperidine-1-carboxylate.

(Z)-Methyl 4-((6-(3-((2,4-dioxothiazolidin-5-ylidene)methyl)phenoxy)-5-methylpyrimidin-4-yl)oxy)piperidine-1-carboxylate.

(Z)-iso-Butyl 4-((6-(3-((2,4-dioxothiazolidin-5-ylidene)methyl)phenoxy)-5-methylpyrimidin-4-yl)oxy)piperidine-1-carboxylate.

(Z)-tert-Butyl 2-(((6-(3-((2,4-dioxothiazolidin-5-ylidene)methyl)phenoxy)-5-methylpyrimidin-4-yl)oxy)methyl)pyrrolidine-1-carboxylate.

(Z)-tert-Butyl-4-((6-(4-((3-(methylsulfonyl)-2,4-dioxothiazolidin-5-ylidene)methyl)phenoxy)pyrimidin-4-yl)oxy)piperidine-1-carboxylate.

(Z)-5-(3-((6-((1-(3-Isopropyl-1,2,4-oxadiazol-5-yl)piperidin-4-yl)oxy)-5-methylpyrimidin-4-yl)oxy)benzylidene)thiazolidine-2,4-dione.

(Z)-5-(3-((6-((1-(5-Ethylpyrimidin-2-yl)piperidin-4-yl)oxy)-5-methylpyrimidin-4-yl)oxy)benzylidene)thiazolidine-2,4-dione.

(Z)-5-(3-((6-((1-Benzylpiperidin-4-yl)oxy)-5-methylpyrimidin-4-yl)oxy)benzylidene)thiazolidine-2,4-dione.

(Z)-5-(3-((5-Methyl-6-((1-(pyrimidin-2-yl)piperidin-4-yl)oxy)pyrimidin-4-yl)oxy)benzylidene)thiazolidine-2,4-dione.

(Z)-Benzyl-4-((6-(3-((2,4-dioxothiazolidin-5-ylidene)methyl)phenoxy)pyrimidin-4-yl)oxy)piperidine-1-carboxylate.

(Z)-Benzyl-4-((6-(4-((2,4-dioxothiazolidin-5-ylidene)methyl)phenoxy)pyrimidin-4-yl)oxy)piperidine-1-carboxylate.
(Z)-tert-Butyl 4-((6-(4-((3-ethyl-2,4-dioxothiazolidin-5-ylidene)methyl)phenoxy)pyrimidin-4-yl)oxy)piperidine-1-carboxylate.
(Z)-Methyl 4-((6-(3-((3-isopropyl-2,4-dioxothiazolidin-5-ylidene)methyl)phenoxy)-5-methylpyrimidin-4-yl)oxy)piperidine-1-carboxylate.
(Z)-Isobutyl 4-((6-(3-((2,4-dioxothiazolidin-5-ylidene)methyl)phenoxy)pyrimidin-4-yl)oxy)piperidine-1-carboxylate.
(Z)-Isobutyl-4-((6-(4-((2,4-dioxothiazolidin-5-yl idene)methyl)phenoxy)pyrimidin-4-yl)oxy)piperidine-1-carboxylate.
(Z)-Methyl-4-((6-(4-((2,4-dioxothiazolidin-5-ylidene)methyl)phenoxy)pyrimidin-4-yl)oxy)piperidine-1-carboxylate.
(Z)-Methyl-4-((6-(3-((2,4-dioxothiazolidin-5-ylidene)methyl)phenoxy)pyrimidin-4-yl)oxy)piperidine-1-carboxylate.
(Z)-5-(4-((6-((1-Benzylpiperidin-4-yl)oxy)pyrimidin-4-yl)oxy)benzylidene)thiazolidine-2,4-dione.
(Z)-5-(4-((6-(1-Benzylpiperidin-4-yl)oxy)-5-methylpyrimidin-4-yl)oxy)benzylidene)thiazolidine-2,4-dione.
(Z)-5-(3-((6-((1-Benzylpiperidin-4-yl)oxy)pyrimidin-4-yl)oxy)benzylidene)thiazolidine-2,4-dione.
(Z)-tert-Butyl 4-((6-((4-(2,4-dioxothiazolidin-5-ylidene)methyl)-2-methoxyphenoxy)pyrimidin-4-yl)oxy)piperidine-1-carboxylate.
(Z)-5-(4-((6-((1-(5-Ethylpyrimidin-2-yl)piperidin-4-yl)oxy)pyrimidin-4-yl)oxy)benzylidene)thiazolidine-2,4-dione.
(Z)-5-(3-((6-((1-(Pyrimidin-2-yl)piperidin-4-yl)oxy)pyrimidin-4-yl)oxy)benzylidene)thiazolidine-2,4-dione.
(Z)-5-(4-((6-((1-(Pyrimidin-2-yl)piperidin-4-yl)oxy)pyrimidin-4-yl)oxy)benzylidene)thiazolidine-2,4-dione.
(Z)-tert-Butyl 4-((6-(3-((2,4-dioxo-3-(2-oxopropyl)thiazolidin-5-ylidene)methyl)phenoxy)-5-methylpyrimidin-4-yl)oxy)piperidine-1-carboxylate.
(Z)-tert-Butyl-4-((6-(3-((3-(2-ethoxy-2-oxoethyl)-2,4-dioxothiazolidin-5-ylidene)methyl)phenoxy)-5-methylpyrimidin-4-yl)oxy)piperidine-1-carboxylate.
(Z)-tert-Butyl-4-((6-(4-((2,4-dioxo-3-(2-oxopropyl)thiazolidin-5-ylidene)methyl)phenoxy)pyrimidin-4-yl)oxy)piperidine-1-carboxylate.
(Z)-5-(3-((6-((1-(5-Chloropyrimidin-2-yl)piperidin-4-yl)oxy)-5-methylpyrimidin-4-yl)oxy)benzylidene)thiazolidine-2,4-dione.
(Z)-5-(3-((6-((1-(5-Bromopyridin-2-yl)piperidin-4-yl)oxy)-5-methylpyrimidin-4-yl)oxy)benzylidene)thiazolidine-2,4-dione.
(3R,4S)-tert-Butyl 4-((6-(3-((Z)-(2,4-dioxothiazolidin-5-ylidene)methyl)phenoxy)-5-methylpyrimidin-4-yl)oxy)-3-fluoropiperidine-1-carboxylate.
(Z)-Benzyl 4-((6-(3-((2,4-dioxothiazolidin-5-yl idene)methyl)phenoxy)-5-methylpyrimidin-4-yl)oxy)piperidine-1-carboxylate.
(Z)-Ethyl-4-((6-(3-((2,4-dioxothiazolidin-5-ylidene)methyl)phenoxy)pyrimidin-4-yl)oxy)piperidine-1-carboxylate.
(Z)-Ethyl-4-((6-(4-((2,4-dioxothiazolidin-5-ylidene)methyl)phenoxy)pyrimidin-4-yl)oxy)piperidine-1-carboxylate.
(Z)-Isobutyl-4-((6-(4-((2,4-dioxothiazolidin-5-ylidene)methyl)phenoxy)pyrimidin-4-yl)oxy)piperidine-1-carboxylate.
(Z)-Isobutyl 4-((6-(3-((2,4-dioxothiazolidin-5-ylidene)methyl)phenoxy)pyrimidin-4-yl)oxy)piperidine-1-carboxylate.
(Z)-5-(3-((6-((1-(5-Ethylpyrimidin-2-yl)piperidin-4-yl)oxy)pyrimidin-4-yl)oxy)benzylidene)thiazolidine-2,4-ione.
(Z)-6-(4-((6-(3-((2,4-Dioxothiazolidin-5-ylidene)methyl)phenoxy)-5-methylpyrimidin-4-yl)oxy)piperidin-1-yl)nicotinonitrile.
(Z)-tert-Butyl-4-((6-(3-((3-benzyl-2,4-dioxothiazolidin-5-ylidene)methyl)phenoxy)-5-methylpyrimidin-4-yl)oxy)piperidine-1-carboxylate.
(Z)-tert-Butyl-4-((6-(3-((3-allyl-2,4-dioxothiazolidin-5-ylidene)methyl)phenoxy)-5-methylpyrimidin-4-yl)oxy)piperidine-1-carboxylate.
(Z)-tert-Butyl-4-((6-(3-((3-(2-bromoethyl)-2,4-dioxothiazolidin-5-yl idene)methyl)phenoxy)-5-methylpyrimidin-4-yl)oxy)piperidine-1-carboxylate.
(Z)-tert-Butyl-4-((6-(3-((3-ethyl-2,4-dioxothiazolidin-5-ylidene)methyl)phenoxy)-5-methylpyrimidin-4-yl)oxy)piperidine-1-carboxylate.
(Z)-3-Ethyl-5-(3-((6-((1-(5-ethylpyrimidin-2-yl)piperidin-4-yl)oxy)-5-methylpyrimidin-4-yl)oxy)benzylidene)thiazolidine-2,4-dione.
(Z)-5-(3-((6-((1-(5-Ethylpyrimidin-2-yl)piperidin-4-yl)oxy)-5-methylpyrimidin-4-yl)oxy)benzylidene)-3-(2-oxopropyl)thiazolidine-2,4-dione.
(Z)-5-(3-((6-((1-(isopropylsulfonyl)piperidin-4-yl)oxy)-5-methylpyrimidin-4-yl)oxy)benzylidene)thiazolidine-2,4-dione.
(Z)-5-(3-((6-((1-acetylpiperidin-4-yl)oxy)pyrimidin-4-yl)oxy)benzylidene)thiazolidine-2,4-dione.
(Z)-5-(4-((6-((1-acetylpiperidin-4-yl)oxy)pyrimidin-4-yl)oxy)benzylidene)thiazolidine-2,4-dione.
(Z)-5-(3-((6-((1-(3-isopropyl-1,2,4-oxadiazol-5-yl)piperidin-4-yl)oxy)pyrimidin-4-yl)oxy)benzylidene)thiazolidine-2,4-dione.
(Z)-5-(3-((6-((1-(3-isopropyl-1,2,4-oxadiazol-5-yl)piperidin-4-yl)oxy)-5-ethylpyrimidin-4-yl)oxy)benzyl idene)-3-methylthiazolidine-2,4-dione.
(Z)-5-(3-((6-((1-(3-isopropyl-1,2,4-oxadiazol-5-yl)piperidin-4-yl)oxy)-5-ethylpyrimidin-4-yl)oxy)benzylidene)-3-(2-oxopropyl)thiazolidine-2,4-dione.
(Z)-3-isopropyl-5-(3-((6-((1-(3-isopropyl-1,2,4-oxadiazol-5-yl)piperidin-4-yl)oxy)-5-methylpyrimidin-4-yl)oxy)benzylidene)thiazolidine-2,4-dione.
(Z)-6-(4-((6-(3-((2,4-dioxothiazolidin-5-ylidene)methyl)phenoxy)pyrimidin-4-yl)oxy)piperidin-1-yl)nicotinonitrile.
(Z)-5-(3-((6-((1-(methylsulfonyl)piperidin-4-yl)oxy)pyrimidin-4-yl)oxy)benzylidene)thiazolidine-2,4-dione.
(Z)-5-(3-((6-((1-(5-chloropyrimidin-2-yl)piperidin-4-yl)oxy)pyrimidin-4-yl)oxy)benzylidene)thiazolidine-2,4-dione.
(Z)-5-(4-((6-((1-(5-chloropyrimidin-2-yl)piperidin-4-yl)oxy)pyrimidin-4-yl)oxy)benzylidene)thiazolidine-2,4-dione.
(Z)-3-(methylsulfonyl)-5-(4-((6-((1-(methylsulfonyl)piperidin-4-yl)oxy)pyrimidin-4-yl)oxy)benzylidene)thiazolidine-2,4-dione.
(Z)-5-(4-((6-((1-(5-bromopyridin-2-yl)piperidin-4-yl)oxy)pyrimidin-4-yl)oxy)benzyl idene)thiazolidine-2,4-dione;
(Z)-5-(3-((6-((1-(5-bromopyridin-2-yl)piperidin-4-yl)oxy)pyrimidin-4-yl)oxy)benzylidene)thiazolidine-2,4-dione.

The novel compounds of this invention may be prepared using the reactions and techniques described in the below section along with, whenever appropriate other suitable processes known to a skilled person. The reactions are performed in solvents appropriate to the reagents and materials employed and are suitable for the transformations being effected. It is understood by those skilled in the art that the nature and order of the synthetic steps presented may be varied for the purpose of optimizing the formation of the compounds of the present invention and also that certain steps may be modified, altered, obvious steps added or deleted in order to optimize as well as required for preparing the compounds of the present invention. Such, obvious changes should also be considered as being part of the present invention.

Scheme: Compounds of general formula (I) where $R_1$, $R_2$, $R_3$, X, Het and n are as defined earlier may be prepared according to the scheme described below.

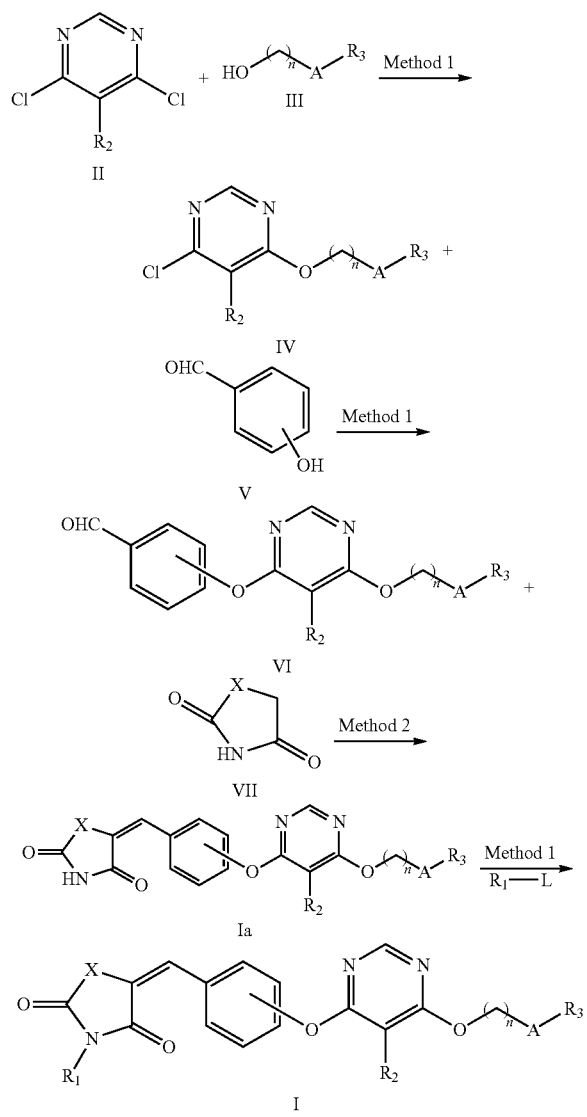

The process of synthesizing the compounds of general formula (I) comprises the steps of i. Reacting compounds of general formula (II), where $R_2$ is as defined earlier with compounds of general formula (III) where all the symbols are as defined earlier to yield compound of general formula (IV);
ii. Reacting compounds of general formula (IV), where all symbols are as defined earlier with (V) to yield compound of general formula (VI);
iii. Reacting compounds of general formula (VI), where all symbols are as defined earlier with compounds of general formula (VII) where all symbols are as defined earlier, to yield compound of general formula (Ia);
iv. Reacting compounds of general formula (Ia), where all symbols are as defined earlier with $R_1$-L, Where L represents a suitable leaving group such as halogen, mesylate, tosylate, triflate & the like to yield compound of general formula (I).

Method 1: The compounds of formula (IV) may be prepared by reacting the compounds of formula (II) with the compounds of formula (III), the compounds of formula (VI) may be prepared by reacting compound of formula (IV) with compound to of formula (V) and the compound of formula (I) may be prepared by reacting compound of formula (Ia) with $R_1$-L under suitable conditions. The reaction may be carried out in presence of solvents such as acetone, tetrahydrofuran, dimethyl sulfoxide, dioxane, acetonitrile, dimethyl formamide, dimethoxy ethane, benzene, toluene, petroleum ether, heptane, hexane, 2-butanone, xylene, alcohols such as methanol, ethanol, propanol, butanol, iso-butanol, tert-butanol, pentanol and the like or mixtures thereof. Bases such as alkali metal carbonates such as $K_2CO_3$, $Na_2CO_3$, $CsCO_3$, and the like, or alkali metal hydroxides such as NaOH, KOH and the like, or alkali metal alkoxides such as tert-BuOK, tert-BuONa and the like, may be used during this reaction. Alkali metal hydrides such as NaH, KH can be used whenever solvent employed is not protic or contain carbonyl group. The reaction may be carried out at a temperature in the range 0° C. to reflux temperature of the solvent(s) used and the reaction time may range from 1 to 48 hours.

Method 2: The compound of formula (Ia) may be prepared by knoevenagel condensation between compound of formula (IV) and compound of formula (VII). The reactions may be carried out in the presence of piperidine and benzoic acid. The reaction may be carried out in presence of solvents such as toluene, benzene and the like or mixture thereof. The reaction may be carried out at reflux temperature of the solvent(s) used and the reaction time may range from 5 to 48 hours.

The following examples further illustrate the processes of preparing compounds of formula (Ia) and (I) according to the present invention and are provided for illustration only. Such disclosure should not be construed as limiting the scope of the present invention in any way.

1H NMR Spectral Data Given In The Examples (Vide Infra) Are Recorded Using a 400 MHz spectrometer (Bruker A VANCE-400) and reported in δ scale. Until and otherwise mentioned the solvent used for NMR is $CDCl_3$. IUPAC system was followed while naming the compounds.

Example 1

(Z)-tert-Butyl 4-((6-(4-((2,4-dioxothiazolidin-5-ylidene)methy l)phenoxy)-5-methylpyrimidin-4-yl)oxy)piperidine-1-carboxylate Step I: Preparation of tert-Butyl 4-((6-chloro-5-methylpyrimidin-4-yl)oxy)piperidine-1-carboxylate Potassium tert-butoxide (3.4 gm, 0.0306 moles) was added to a solution of tert-butyl 4-hydroxypiperidine-1-carboxylate (6.8 gm, 0.0368 moles) and 4,6-dichloro-5-methylpyrimidine (5.0 gm, 0.0368 moles) in dry THF at 0° C. and the reaction mixture was stirred for 15-20 hours at 30° C. The reaction mixture was poured into ice cold water and extracted with ethyl acetate. The organic extract was washed with water and brine, dried over sodium sulfate and evaporated under reduced pressure to collect 5.1 gm off-white solid product.

$^1$HNMR: δ 1.47 (s, 9H), 1.73-1.80 (m, 2H), 1.94-2.0 (m, 2H), 2.22 (s, 3H), 3.32-3.39 (m, 2H), 3.68-3.74 (m, 2H), 5.31-5.35 (m, 1H), 8.38 (s, 1H).

Step II. tert-Butyl 4-((6-(4-formylphenoxy)-5-methylpyrimidin-4-yl)oxy)piperidine-1-carboxylate To a solution of t-butyl 4-((6-chloro-5-methylpyrimidin-4-yl)oxy)piperidine-1-carboxylate (2.0 gm, 0.00610 mole) and 4-hydroxybenzaldehyde (1.34 gm, 0.00610 mole) in dimethyl formamide (50 mL), Cesium carbonate (4 gm, 0.0122 mole) was added and reaction mixture was stirred for 24 hours at 70° C. Then reaction mixture was cooled, poured into ice cold water and extracted with ethyl acetate. organic extract was washed with water and brine, dried over sodium sulfate and evaporated under reduced pressure to yield crude product. The crude product so obtained was purified through column chromatography using 15-20% ethyl acetate in hexane to yield 1 gm product as oil.

$^1$HNMR: δ 1.48 (s, 9H), 1.75-1.81 (m, 2H), 1.96-2.01 (m, 2H), 2.18 (s, 3H), 3.34-3.41 (m, 2H), 3.70-3.76 (m, 2H), 5.32-5.36 (m, 1H), 7.27-7.29 (m, 2H), 7.93-7.96 (m, 2H), 8.25 (s, 1H), 9.99 (s, 1H).

Step III. (Z)-tert-Butyl 4-((6-(4-((2,4-dioxothiazolidin-5-ylidene)methyl)phenoxy)-5-methylpyrimidin-4-yl)oxy)piperidine-1-carboxylate To a solution of tert-butyl 4-((6-(4-formylphenoxy)-5-methylpyrimidin-4-yl)oxy)piperidine-1-carboxylate (950 mg, 0.002298 mole), thiazolidine-2,4-dione (241 mg, 0.00206 mole) and benzoic acid (0.0364 mg, 0.000298 mole) in toluene (30 ml), piperidine (0.033 ml, 0.00344 mole) was added and reaction mixture was refluxed for 7 hours using Dean-Stark apparatus. Then reaction mixture was cooled to 30° C. and solid product was filtered, washed with ice cold toluene and dried to yield 700 mg white solid product.

$^1$HNMR: δ 1.46 (s, 9H), 1.76-1.83 (m, 2H), 1.97-2.02 (m, 2H), 2.18 (s, 3H), 3.35-3.41 (m, 2H), 3.71-3.75 (m, 2H), 5.33-5.37 (m, 1H), 7.22-7.25 (m, 2H), 7.53 (d, J=8.4 Hz, 2H), 7.77 (s, 1H), 8.25 (s, 1H).

Example 2

(Z)-tert-Butyl 4-((6-(4-((3-(2-ethoxy-2-oxoethyl)-2,4-dioxothiazolidin-5-ylidene)methyl)phenoxy)-5-methylpyrimidin-4-yl)oxy)piperidine-1-carboxylate To a solution of tert-butyl 4-((6-(4-((2,4-dioxothiazolidin-5-ylidene)methyl)phenoxy)-5-methylpyrimidin-4-yl)oxy)piperidine-1-carboxylate (250 mg, 0.0004882 mole) in dimethyl formamide (10 ml), sodium hydride (50%, 23.4 mg, 0.0004882 mole) was added at 0° C. and reaction mixture was stirred for 1 hours 30° C. and then ethyl bromoacetate (0.08 ml, 0.000733 mole) was added at 0° C., then reaction mixture was stirred for 3 hours at 30° C. Then reaction mixture was poured into ice cold water and extracted with ethyl acetate. Organic extract was washed with water and brine, dried over sodium sulfate and evaporated under reduced pressure to yield crude product. Then crude product was purified through column chromatography using 18% ethyl acetate in hexane as an eluent to yield the product as white solid (160 mg).

$^1$HNMR: δ 1.30 (t, J=7.0 Hz, 3H), 1.48 (s, 9H), 1.76-1.81 (m, 2H), 1.96-2.01 (m, 2H), 2.18 (s, 3H), 3.34-3.41 (m, 2H), 3.71-3.76 (m, 2H), 4.25 (q, J=7.2 Hz, 2H), 4.48 (s, 2H), 5.33-5.35 (m, 1H), 7.55 (d, J=9.6 Hz, 2H), 7.57 (d, J=8.4 Hz, 2H), 7.93 (s, 1H), 8.25 (s, 1H).

Example 3

(Z)-5-(4-((6-((1-(5-Ethylpyrimidin-2-yl)piperidin-4-yl)oxy)-5-methylpyrimidin-4-yl)oxy)benzylidene)-3-(methylsulfonyl)thiazolidine-2,4-dione To an ice-cold solution of –5-(4-((6-((1-(5-ethylpyrimidin-2-yl)piperidin-4-yl)oxy)-5-methylpyrimidin-4-yl)oxy)benzylidene)thiazolidine-2,4-dione (145 mg, 0.0002799 mole) in dichloromethane (5 ml), triethylamine (0.05 ml, 0.000335 mole) was added followed by methane sulfonyl chloride (0.03 ml, 0.0004198 mole) and stirred below 30° C. for 3 hours. The reaction mixture was diluted with dichloromethane (20 ml), washed with water, dried over calcium chloride and evaporated on a rotavpour under reduced pressure to yield crude product. Then crude product was purified using column chromatography using 30% ethyl acetate in hexane as an eluent to yield the product as yellow solid (17 mg).

$^1$HNMR: δ 1.27 (t, J=7.6 Hz, 3H), 1.64-1.72 (m, 2H), 1.97-2.02 (m, 2H), 2.43 (q, J=7.2 Hz, 2H), 2.49 (s, 3H), 3.59-3.63 (m, 2H), 3.65 (m, 3H), 4.06-4.12 (m, 2H), 5.37-5.41 (m, 1H), 7.31-7.36 (m, 2H), 7.64-7.70 (m, 2H), 8.00 (s, 1H), 8.26 (s, 2H), 8.28 (s, 1H).

Example 4

(Z)-Ethyl-4-((5-methyl-6-(3-((3-methyl-2,4-dioxothiazoldin-5-ylidene)methy l)phenoxy)pyrimidin-4-yl)oxy)piperidine-1-carboxylate To a solution (Z)-ethyl 4-((6-(3-((2,4-dioxothiazolidin-5-ylidene)methyl)phenoxy)-5-methylpyrimidin-4-yl)oxy)piperidine-1-carboxylate (300 mg, 0.0006198 mole) in dimethyl acetamide (10 ml), $K_2CO_3$ (171 mg, 0.001239 mole) was added followed by addition of methyl iodide (0.060 ml, 0.0009297 mole) at 0° C. and reaction mixture was stirred at 27° C. for 30 minutes. Then reaction mixture was poured into ice cold water and extracted with ethyl acetate. Organic layer was washed with water and brine, dried over sodium sulfate and evaporated on a rotavpour to yield the product as yellow solid (300 mg).

$^1$HNMR: δ 1.28 (t, J=6.8 Hz, 3H), 1.79-1.83 (m, 2H), 1.98-2.03 (m, 2H), 2.19 (s, 3H), 3.25 (s, 3H), 3.42-3.48 (m, 2H), 3.74-3.79 (m, 2H), 4.16 (q, J=7.2 Hz, 2H), 5.35-5.37 (m, 1H), 7.18-7.21 (m, 1H), 7.26-7.29 (m, 1H), 7.37 (d, J=7.6 Hz, 1H), 7.51 (t, J=8.0 Hz, 1H), 7.89 (s, 1H), 8.24 (s, 1H).

Example 5

(Z)-5-(3-((5-Methyl-6-((1-(methylsulfonyl)piperidin-4-yl)oxy)pyrimidin-4-yl)oxy)benzylidene)thiazolidine-2,4-dione Step 1: Trifluoro acetate salt of (Z)-5-(3-((5-methyl-6-(piperidin-4-yloxy)pyrimidin-4-yl)oxy)benzylidene)thiazolidine-2,4-dione To a solution of (Z)-tert-Butyl 4-((6-(3-((2,4-dioxothiazolidin-5-ylidene)methyl)phenoxy)-5-methylpyrimidin-4-yl)oxy)piperidine-1-carboxylate (500 mg, mole) in dichloromethane, trifluoroacetic acid (2 ml) was added and reaction mixture was stirred for 6 hrs at 30° C. Then reaction mixture was concentrated under reduced pressure to collect the crude product as thick liquid and product was used for next step of synthesis.

Step 2: (Z)-5-(3-((5-Methyl-6-((1-(methylsulfonyl) piperidin-4-yl)oxy)pyrimidin-4-yl)oxy)benzylidene) thiazolidine-2,4-dione To a solution Trifluoro acetate salt of (Z)-5-(3-((5-methyl-6-(piperidin-4-yloxy)pyrimidin-4-yl)oxy)benzylidene)thiazolidine-2,4-dione (524 mg, 0.000974 mol) in dichloromethane (20 ml), was added triethyl amine (1.35 ml, 0.00974 mol) followed by methane sulfonyl chloride (0.150 ml, 0.001461 mol) at 0° C. and reaction mixture was stirred for 2 hrs at 30° C. Then reaction mixture was diluted with dichloromethane and washed with water, dried over calcium chloride and evaporated under reduced pressure to collect the crude product. Then the crude product was purified by column chromatography using 1% methanol in chloroform as eluent to yield 300 mg product as white solid.

$^1$HNMR (DMSO-d6): δ 1.83-1.86, (m, 2H), 2.03-2.08 (m, 2H), 2.15 (s, 3H), 2.92 (s, 3H), 3.18-3.23 (m, 2H), 3.33-3.36 (m, 2H), 5.25-5.30 (m, 1H), 7.27 (dd, J=7.6 & 1.6 Hz, 1H), 7.40 (d, J=2.0 Hz, 1H), 7.46 (d, J=8.8 Hz, 1H), 5.58 (t, J=8.0 Hz, 1H), 7.79 (s, 1H), 8.31 (s, 1H), 12.65 (s, 1H).

Example 6

(Z)-5-(3-((6-((1-Acetylpiperidin-4-yl)oxy)-5-methylpyrimidin-4-yl)oxy)benzylidene)thiazolidine-2,4-dione To a solution Trifluoro acetate salt of (Z)-5-(3-((5-methyl-6-(piperidin-4-yloxy)pyrimidin-4-yl)oxy)benzylidene)thiazolidine-2,4-dione prepared in step 1 of example 5 (524 mg, 0.000974 mol) in dichloromethane (20 ml), triethyl amine (1.35 ml, 0.00974 mol) was added followed by the addition of acetyl chloride (0.104 ml, 0.001461 mol) at 0° C. and the reaction mixture was stirred for 5 hrs at 30° C. Then reaction mixture was diluted with dichloromethane, washed with water, dried over calcium chloride and evaporated under reduced pressure to collect the crude product. The crude product was then purified by column chromatography using 1.5% methanol in chloroform as eluent to yield the 300 mg product as yellow solid.

$^1$HNMR (DMSO-d6): δ 1.59-1.65 (m, 1H), 1.70-1.75 (m, 1H), 1.89-1.98 (m, 1H), 2.00-2.03 (m, 1H), 2.14 (s, 3H), 2.17 (s, 3H), 3.39-3.43 (m, 2H), 3.64-3.68 (m, 1H), 3.72-3.77 (m, 1H), 5.33-5.37 (m, 1H), 7.29 (dd, J=7.60 & 1.60 Hz, 1H), 7.40 (d, J=3.6 Hz, 1H), 7.46 (d, J=8.0 Hz, 1H), 7.58 (t, J=7.6 Hz, 1H), 7.79 (s, 1H), 8:27 (s, 1H), 12.65 (s, 1H, exchangeable).

The following compounds are prepared by procedure similar to any one of those described in above examples or suitable combinations of the processes along with appropriate variations in reactants, reaction conditions and quantities of reagents etc. as are well within the scope of a skilled person.

Example 7

(Z)-5-(4-((6-((1-(3-iso-Propyl-1,2,4-oxadiazol-5-yl) piperidin-4-yl)oxy)-5-methylpyrimidin-4-yl)oxy) benzylidene)thiazolidine-2,4-dione $^1$HNMR: δ 1.30 (d, J=7.2 Hz, 6H), 1.92-1.99 (m, 2H), 2.08-2.14 (m, 2H), 2.19 (s, 3H), 2.89-2.94 (m, 1H), 3.62-3.68 (m, 2H), 3.83-3.89 (m, 2H), 5.42-5.46 (m, 1H), 7.23-7.27 (m, 2H), 7.54 (d, J=8.4 Hz, 2H), 7.80 (s, 1H), 8.26 (s, 1H).

Example 8

(Z)-tert-Butyl 4-((6-(4-((2,4-dioxothiazolidin-5-ylidene)methyl)-2-methoxyphenoxy)-5-methylpyrimidin-4-yl)oxy)piperidine-1-carboxylate $^1$HNMR: δ 1.48 (s, 9H), 1.78-1.97 (m, 2H), 1.97-2.02 (m, 2H), 2.21 (s, 3H), 3.35-3.42 (m, 2H), 3.72-3.73 (m, 2H), 3.81 (m, 3H), 5.31-5.36 (m, 1H), 7.05 (d, J=1.6 Hz, 1H), 7.12 (, dd, J=8.0 & 1.6 Hz, 1H), 7.21 (d, J=8.4 Hz, 1H), 7.69 (s, 1H), 8.18 (s, 1H).

Example 9

(Z)-tert-Butyl 4-((6-(3-((2,4-dioxothiazolidin-5-ylidene)methyl)phenoxy)-5-methylpyrimidin-4-yl) oxy)piperidine-1-carboxylate $^1$HNMR: δ 1.46 (s, 9H), 1.76-1.83 (m, 2H), 1.97-2.02 (m, 2H), 2.19 (s, 3H), 3.35-3.42 (m, 2H), 3.71-3.75 (m, 2H), 5.33-3.36 (m, 1H), 7.19-7.21 (m, 1H), 7.26-7.27 (m, 1H), 7.36 (d, J=8 Hz, 1H), 7.51 (t, J=5.2 Hz, 1H), 7.81 (s, 1H), 8.24 (s, 1H).

Example 10

(Z)-5-(4-((6-((1-(3-iso-Propyl-1,2,4-oxadiazol-5-yl) piperidin-4-yl)oxy)pyrimidin-4-yl)oxy)benzylidene) thiazolidine-2,4-dione $^1$HNMR: δ 1.30 (d, J=7.2 Hz, 6H), 1.75-1.80 (m, 2H), 2.04-2.09 (m, 2H), 2.77-2.84 (m, 1H), 3.45-3.52 (m, 2H), 3.76-3.82 (m, 2H), 5.30-5.34 (m, 1H), 6.48 (s, 1H), 7.35 (d, J=6.8 & 2.0 Hz, 2H), 7.67 (d, J=8.8 Hz, 2H), 7.82 (s, 1H), 8.47 (s, 1H), 12.63 (s, 1H).

Example 11

(Z)-Methyl 4-((6-(4-((2,4-dioxothiazolidin-5-ylidene)methyl)phenoxy)-5-methylpyrimidin-4-yl) oxy)piperidine-1-carboxylate $^1$HNMR: 1.79-1.83 (m, 2H), 1.98-2.03 (m, 2H), 2.19 (s, 3H), 3.43-3.48 (m, 2H), 3.72 (s, 3H), 3.73-3.79 (m, 2H), 5.35-5.39 (m, 1H), 7.21-7.26 (m, 2H), 7.53 (dd, J=6.8 & 2.0 Hz, 2H), 7.77 (s, 1H), 8.25 (s, 1H).

Example 12

(Z)-tert-Butyl 4-((6-(4-((2,4-dioxothiazolidin-5-ylidene)methyl)phenoxy)pyrimidin-4-yl)oxy)piperidine-1-carboxylate $^1$HNMR: δ 1.47 (s, 9H), 1.70-1.78 (m, 2H), 1.97-2.01 (m, 2H), 3.25-3.31 (m, 2H), 3.71-3.80 (m, 2H), 5.29-5.33 (m, 1H), 6.24 (s, 1H), 7.23-7.26 (m, 2H), 7.53-7.56 (m, 2H), 7.81 (s, 1H), 8.42 (s, 1H).

Example 13

(Z)-Benzyl 4-((6-(4-((2,4-dioxothiazolidin-5-ylidene)methyl)phenoxy)-5-methylpyrimidin-4-yl) oxy)piperidine-1-carboxylate $^1$HNMR: δ 1.63-1.71 (m, 2H), 1.93-1.98 (m, 2H), 2.11 (s, 3H), 3.31-3.37 (m, 2H), 3.60-3.66 (m, 2H), 5.08 (s, 2H), 5.30-5.33 (m, 1H), 7.31 (d, J=8.8 Hz, 2H), 7.35-7.39 (m, 5H), 7.63-7.65 (m, 2H), 7.81 (s, 1H), 8.27 (s, 1H), 12.61 (s, 1H).

Example 14

(Z)-Ethyl 4-((6-(4-((2,4-dioxothiazolidin-5-ylidene)methyl)phenoxy)-5-methylpyrimidin-4-yl)oxy)piperidine-1-carboxylate $^1$HNMR: δ 1.81 (t, J=7.0 Hz, 3H), 1.62-1.69 (m, 2H), 1.91-1.96 (m, 2H), 2.11 (s, 3H), 3.31-3.37 (m, 2H), 3.60-3.66 (m, 2H), 4.03 (q, J=7.2 Hz, 2H), 5.27-5.33 (m, 1H), 7.31 (d, J=8.8 Hz, 2H), 7.64 (d, J=8.8 Hz, 2H), 7.80 (s, 1H), 8.26 (s, 1H), 12.6 (s, 1H).

Example 15

(Z)-iso-Butyl 4-((6-(4-((2,4-dioxothiazolidin-5-ylidene)methyl)phenoxy)-5-methylpyrimidin-4-yl)oxy)piperidine-1-carboxylate $^1$HNMR: δ 0.89 (d, J=6.8 Hz, 6H), 1.62-1.69 (m, 2H), 1.83-1.90 (m, 1H), 1.93-1.97 (m, 2H), 2.11 (s, 3H), 3.30-3.35 (m, 2H), 3.60-3.66 (m, 2H), 3.79 (d, J=6.4 Hz, 2H), 5.30-5.33 (m, 1H), 7.31 (d, J=8.8 Hz, 2H), 7.65 (d, J=8.8 Hz, 2H), 7.81 (s, 1H), 8.27 (s, 1H), 12.61 (s, 1H).

Example 16

(Z)-iso-Propyl 4-((6-(4-((2,4-dioxothiazolidin-5-ylidene)methyl)phenoxy)-5-methylpyrimidin-4-yl)oxy)piperidine-1-carboxylate $^1$HNMR: δ 1.18 (d, J=6.0 Hz, 6H), 1.61-1.68 (m, 2H), 1.91-1.96 (m, 2H), 2.11 (s, 3H), 3.30-3.35 (m, 2H), 3.60-3.66 (m, 2H), 4.74-4.80 (m, 1H), 5.29-5.32 (m, 1H), 7.31 (d, J=8.4 Hz, 2H), 7.65 (d, J=8.8 Hz, 2H), 7.81 (s, 1H), 8.27 (s, 1H), 12.6 (s, 1H).

Example 17

(Z)-5-(4-((5-Methyl-6-((1-(pyrimidin-2-yl)piperidin-4-yl)oxy)pyrimidin-4-yl)oxy)benzylidene)thiazolidine-2,4-dione $^1$HNMR: δ 1.67-1.71 (m, 2H), 1.98-2.03 (m, 2H), 2.12 (s, 3H), 3.64-3.70 (m, 2H), 4.08-4.13 (m, 2H), 5.39-5.40 (m, 1H), 6.61 (t, J=8.0 Hz, 1H), 7.31-7.33 (m, 2H), 7.64-7.66 (m, 2H), 7.80 (s, 1H), 8.28 (s, 1H), 8.35 (s, 2H), 12.6 (s, 1H).

Example 18

(Z)-tert-Butyl 2-(((6-(4-((2,4-dioxothiazolidin-5-ylidene)methyl)phenoxy)-5-methylpyrimidin-4-yl)oxy)methyl)pyrrolidine-1-carboxylate $^1$HNMR: δ 1.47 (s, 9H), 1.88-2.04 (m, 4H), 2.19 (s, 3H), 3.39-3.48 (m, 2H), 4.15-4.27 (m, 1H), 4.38-4.40 (m, 1H), 4.48-4.52 (m, 1H), 7.22 (d, J=8.4 Hz, 2H), 7.52 (d, J=8.8 Hz, 2H), 7.76 (s, 1H), 8.25 (s, 1H), 9.33 (s, 1H).

Example 19

(Z)-tert-Butyl 4-((6-(3-((2,4-dioxothiazolidin-5-ylidene)methyl)phenoxy)pyrimidin-4-yl)oxy)piperidine-1-carboxylate $^1$HNMR: δ 1.47 (s, 9H), 1.70-1.78 (m, 2H), 1.97-2.01 (m, 2H), 3.25-3.32 (m, 2H), 3.76-3.80 (m, 2H), 5.28-5.32 (m, 1H), 6.20 (s, 1H), 7.21-7.24 (m, 1H), 7.28-7.29 (m, 1H), 7.39 (d, J=8.0 Hz, 1H), 7.53 (t, J=8.0 Hz, 1H), 7.82 (s, 1H), 8.41 (s, 1H).

Example 20

(Z)-Ethyl 4-((6-(3-((2,4-dioxothiazolidin-5-ylidene)methyl)phenoxy)-5-methylpyrimidin-4-yl)oxy)piperidine-1-carboxylate $^1$HNMR: δ 1.26 (t, J=10.4 Hz, 3H), 1.77-1.85 (m, 2H), 1.98-2.04 (m, 2H), 2.19 (s, 3H), 3.42-3.48 (m, 2H), 3.75-3.79 (m, 2H), 4.17 (q, J=6.8 Hz, 2H), 5.34-3.39 (m, 1H), 7.18-7.21 (m, 1H), 7.26-7.28 (m, 1H), 7.36 (d, J=8 Hz, 1H), 7.51 (t, J=5.2 Hz, 1H), 7.79 (s, 1H), 8.24 (s, 1H), 9.15 (s, 1H).

Example 21

(Z)-Methyl 4-((6-(3-((2,4-dioxothiazolidin-5-ylidene)methyl)phenoxy)-5-methylpyrimidin-4-yl)oxy)piperidine-1-carboxylate $^1$HNMR: δ 1.79-1.85 (m, 2H), 1.98-2.03 (m, 2H), 2.19 (s, 3H), 3.44-3.48 (m, 2H), 3.72 (s, 3H), 3.75-3.76 (m, 2H), 5.35-3.38 (m, 1H), 7.18-7.21 (m, 2H), 7.26-7.28 (m, 1H), 7.36 (d, J=8.0 Hz, 1H), 7.51 (t, J=5.2 Hz, 1H), 7.80 (s, 1H), 8.24 (s, 1H).

Example 22

(Z)-iso-Butyl 4-((6-(3-((2,4-dioxothiazolidin-5-ylidene)methyl)phenoxy)-5-methylpyrimidin-4-yl)oxy)piperidine-1-carboxylate $^1$HNMR: δ 0.95 (d, J=6.4 Hz, 6H), 1.78-1.86 (m, 2H), 1.90-2.04 (m, 3H), 2.19 (s, 3H), 3.43-3.49 (m, 2H), 3.75-3.81 (m, 2H), 3.89 (d, J=6.8 Hz, 2H), 5.34-5.40 (m, 1H), 7.19 (m, 1H), 7.26-7.35 (m, 1H), 7.36 (d, J=8.0 Hz, 1H), 7.51 (t, J=8.0 Hz, 1H), 7.80 (s, 1H), 8.24 (s, 1H), 8.78 (s, 1H).

Example 23

(Z)-tert-Butyl 2-(((6-(3-((2,4-dioxothiazolidin-5-ylidene)methyl)phenoxy)-5-methylpyrimidin-4-yl)oxy)methyl)pyrrolidine-1-carboxylate $^1$HNMR: δ 1.47 (s, 9H), 1.86-2.04 (m, 4H), 2.19 (s, 3H), 3.39-3.49 (m, 2H), 4.11-4.27 (m, 1H), 4.38-4.40 (m, 1H), 4.48-4.51 (m, 1H), 7.18-7.20 (m, 1H), 7.26-7.27 (m, 1H), 7.35 (d, J=7.6 Hz, 1H), 7.51 (t, J=8.0 Hz, 1H), 7.79 (s, 1H), 8.24 (s, 1H), 9.10 (s, 1H).

Example 24

(Z)-tert-Butyl 4-((6-(4-((3-(methylsulfonyl)-2,4-dioxothiazolidin-5-ylidene)methyl)phenoxy)pyrimidin-4-yl)oxy)piperidine-1-carboxylate $^1$HNMR: δ 1.47 (s, 9H), 1.70-1.78 (m, 2H), 1.97-2.01 (m, 2H), 3.25-3.31 (m, 2H), 3.54 (m, 3H), 3.71-3.80 (m, 2H), 5.29-5.33 (m, 1H), 6.25 (s, 1H), 7.29 (dd, J=6.8 & 2.0 Hz, 2H), 7.56 (d, J=8.8 Hz, 2H), 7.96 (s, 1H), 8.42 (s, 1H).

Example 25

(Z)-5-(3-((6-((1-(3-Isopropyl-1,2,4-oxadiazol-5-yl)piperidin-4-yl)oxy)-5-methylpyrimidin-4-yl)oxy)benzylidene)thiazolidine-2,4-dione ¹HNMR: δ 130 (d, J=7.2 Hz, 6H), 1.93-2.00 (m, 2H), 2.08-2.15 (m, 2H), 2.20 (s, 3H), 2.87-2.94 (m, 1H), 3.62-3.68 (m, 2H), 3.83-3.89 (m, 2H), 5.42-5.46 (m, 1H), 7.20-7.22 (m, 1H), 7.27-7.28 (m, 1H), 7.36 (d, J=7.6 Hz, 1H), 7.52 (t, J=8.0 Hz, 1H), 7.82 (s, 1H), 8.25 (s, 1H), 8.35 (broad singlet, 1H).

Example 26

(Z)-5-(3-((6-((1-(5-Ethylpyrimidin-2-yl)piperidin-4-yl)oxy)-5-methylpyrimidin-4-yl)oxy)benzylidene)thiazolidine-2,4-dione ¹HNMR: δ 1.27 (t, J=7.6 Hz, 3H), 1.82-1.90 (m, 2H), 2.05-2.12 (m, 2H), 2.19 (s, 3H), 2.48 (q, J=7.6 Hz, 2H), 3.68-3.74 (m, 2H), 4.15-4.21 (m, 2H), 5.41-5.47 (m, 1H), 7.19-7.22 (m, 1H), 7.26-7.29 (m, 1H), 7.36 (d, J=8.10 Hz, 1H), 7.51 (t, J=8.0 Hz, 1H), 7.80 (s, 1H), 8.20 (s, 2H), 8.26 (s, 1H).

Example 27

(Z)-5-(3-((6-((1-Benzylpiperidin-4-yl)oxy)-5-methylpyrimidin-4-yl)oxy)benzylidene)thiazolidine-2,4-dione ¹HNMR: δ 1.87-1.95 (m, 2H), 2.08-2.14 (m, 2H), 2.16 (s, 3H), 2.49-2.51 (m, 2H), 2.79-2.81 (m, 2H), 3.63 (s, 2H), 5.20-5.24 (m, 1H), 7.17-7.20 (m, 1H), 7.26-7.38 (m, 7H), 7.50 (t, J=8.0 Hz, 1H), 7.79 (s, 1H), 8.22 (s, 1H).

Example 28

(Z)-5-(3-((5-Methyl-6-((1-(pyrimidin-2-yl)piperidin-4-yl)oxy)pyrimidin-4-yl)oxy)benzylidene)thiazolidine-2,4-dione ¹HNMR: δ 1.68-1.91 (m, 2H), 2.06-2.13 (m, 2H), 2.20 (s, 3H), 3.73-3.79 (m, 2H), 4.18-4.24 (m, 2H), 5.43-5.48 (m, 1H), 6.49 (t, J=9.6 Hz, 1H), 7.13-7.29 (m, 2H), 7.36 (d, J=8.0 Hz, 1H), 7.52 (t, J=8.10 Hz, 1H), 7.81 (s, 1H), 8.26 (s, 1H), 8.32 (d, J=4.4 Hz, 2H).

Example 29

(Z)-Benzyl 4-((6-(3-((2,4-dioxothiazolidin-5-ylidene)methyl)phenoxy)pyrimidin-4-yl)oxy)piperidine-1-carboxylate ¹HNMR: δ 1.78 (bs, 2H), 2.00 (bs, 2H), 3.37-3.43 (m, 2H), 3.82-3.85 (m, 2H), 5.15 (s, 2H), 5.30-5.36 (m, 1H), 6.21 (s, 1H), 7.22 (dd, J=7.6 & 1.6 Hz, 1H), 7.26-7.30 (m, 1H, 7.31-7.40 (m, 6H), 7.53 (t, J=8.0 Hz, 1H), 7.81 (s, 1H), 8.41 (s, 1H), 8.61 (s, 1H).

Example 30

(Z)-Benzyl 4-((6-(4-((2,4-dioxothiazolidin-5-ylidene)methyl)phenoxy)pyrimidin-4-yl)oxy)piperidine-1-carboxylate ¹HNMR: δ 1.78 (bs, 2H), 2.00 (bs, 2H), 3.37-3.43 (m, 2H), 3.82-3.85 (m, 2H), 5.15 (s, 2H), 5.30-5.36 (m, 1H), 6.24 (s, 1H), 7.23-7.26 (m, 2H), 7.30-7.39 (m, 5H), 7.53-7.56 (m, 2H), 7.81 (s, 1H), 8.41 (s, 1H).

Example 31

(Z)-tert-Butyl 4-((6-(4-((3-ethyl-2,4-d oxothiazolidin-5-ylidene)methyl)phenoxy)pyrimidin-4-yl)oxy)piperidine-1-carboxylate ¹HNMR: δ 1.28 (t, J=7.2 Hz, 3H), 1.47 (s, 9H), 1.71-1.76 (m, 2H), 1.96-2.01 (m, 2H), 3.24-3.31 (m, 2H), 3.76-3.85 (m, 4H), 5.28-5.32 (m, 1H), 6.21 (s, 1H), 7.23-7.27 (m, 2H), 7.55-7.58 (m, 2H), 7.89 (s, 1H), 8.42 (s, 1H).

Example 32

(Z)-Methyl 4-((6-(3-((3-isopropyl-2,4-dioxothiazolidin-5-ylidene)methyl)phenoxy)-5-methylpyrimidin-4-yl)oxy)piperidine-1-carboxylate ¹HNMR: δ 1.48 (d, J=7.2 Hz, 6H), 1.79-1.83 (m, 2H), 1.98-2.03 (m, 2H), 2.19 (s, 3H), 3.43-3.49 (m, 2H), 3.72 (s, 3H), 3.74-3.76 (m, 2H), 4.63-4.70 (m, 1H), 5.33-3.39 (m, 1H), 7.16-7.19 (m, 1H), 7.26-7.29 (m, 1H), 7.36 (d, J=7.6 Hz, 1H), 7.51 (t, J=8.0 Hz, 1H), 7.82 (s, 1H), 8.24 (s, 1H).

Example 33

(Z)-Isobutyl 4-((6-(3-((2,4-dioxothiazolidin-5-ylidene)methyl)phenoxy)pyrimidin-4-yl)oxy)piperidine-1-carboxylate ¹HNMR: δ 0.94 (d, J=6.8 Hz, 6H), 1.72-1.81 (m, 2H), 1.89-2.04 (m, 3H), 3.34-3.49 (m, 2H), 3.81-3.84 (m, 2H), 3.88 (d, J=6.4 Hz, 2H), 5.29-5.36 (m, 1H), 6.21 (s, 1H), 7.22 (dd, J=8.0 & 1.6 Hz, 1H), 7.26-7.29 (m, 1H), 7.39 (d, J=8.0 Hz, 1H), 7.53 (t, J=8.0 Hz, 1H), 7.81 (s, 1H), 8.88 (s, 1H).

Example 34

(Z)-Isobutyl 4-((6-(4-((2,4-dioxothiazolidin-5-ylidene)methyl)phenoxy)pyrimidin-4-yl)oxy)piperidine-1-carboxylate ¹HNMR: δ 0.94 (d, J=6.4 Hz, 6H), 1.72-1.81 (m, 2H), 1.90-2.03 (m, 3H), 3.34-3.40 (m, 2H), 3.81-3.85 (m, 2H), 3.88 (d, J=6.8 Hz, 2H), 5.30-5.36 (m, 1H), 6.25 (s, 1H), 7.23-7.26 (m, 2H), 7.55 (d, J=8.8 & 2.0 Hz, 2H), 7.80 (s, 1H), 8.42 (s, 1H).

Example 35

(Z)-Methyl 4-((6-(4-((2,4-dioxothiazolidin-5-ylidene)methyl)phenoxy)pyrimidin-4-yl)oxy)piperidine-1-carboxylate ¹HNMR: δ 1.68-1.80 (m, 2H), 1.98-2.03 (m, 2H), 3.34-3.40 (m, 2H), 3.71 (s, 3H), 3.79 (bs, 2H), 5.30-5.36 (m, 1H), 6.25 (s, 1H), 7.23-7.26 (m, 2H), 7.53-7.56 (m, 2H), 7.81 (s, 1H), 8.42 (s, 1H).

Example 36

(Z)-Methyl 4-((6-(3-((2,4-dioxothiazolidin-5-ylidene)methyl)phenoxy)pyrimidin-4-yl)oxy)piperidine-1-carboxylate ¹HNMR: δ 1.72-1.80 (m, 2H), 1.98-2.02 (m, 2H), 3.34-3.40 (m, 2H), 3.71 (s, 3H), 3.75-3.81 (m, 2H), 5.30-5.34 (m, 1H), 6.20 (s, 1H), 7.20-7.23 (m, 1H), 7.27 (dd, J=4.0 & 2.0 Hz, 1H), 7.36 (d, J=8.0 Hz, 1H), 7.51 (t, J=8.0 Hz, 1H), 7.80 (s, 1H), 8.41 (s, 1H).

Example 37

(Z)-5-(4-((6-((1-Benzylpiperidin-4-yl)oxy)pyrimidin-4-yl)oxy)benzylidene)thiazolidine-2,4-dione ¹HNMR: δ 1.83-1.93 (m, 2H), 2.07-2.12 (m, 2H), 2.44-2.48 (m, 2H), 2.84-2.87 (m, 2H), 3.65 (s, 2H), 5.16-5.20 (m, 1H), 6.19 (s, 1H), 7.22-7.51 (m, 7H), 7.51-7.56 (m, 2H), 7.77 (s, 1H), 8.41 (s, 1H).

Example 38

(Z)-5-(4-((6-((1-Benzylpiperidin-4-yl)oxy)-5-methylpyrimidin-4-yl)oxy)benzylidene)thiazolidine-2,4-dione ¹HNMR: δ 1.86-1.95 (m, 2H), 2.07-2.14 (m, 2H), 2.16 (s, 3H), 2.46-2.50 (m, 2H), 2.79-2.87 (m, 2H), 3.63 (s, 2H), 5.21-5.24 (m, 1H), 7.20-7.23 (m, 1H), 7.26-7.36 (m, 5H), 7.51-7.55 (m, 2H), 7.74 (s, 1H), 8.23 (s, 1H).

Example 39

(Z)-5-(3-((6-((1-Benzylpiperidin-4-yl)oxy)pyrimidin-4-yl)oxy)benzylidene)thiazolidine-2,4-dione ¹HNMR: δ 1.86-1.96 (m, 2H), 2.10-2.16 (m, 2H), 2.56-2.59 (m, 2H), 2.89-2.90 (m, 2H), 3.73 (s, 2H), 5.16-5.20 (m, 1H), 6.15 (s, 1H), 7.17-7.20 (m, 1H), 7.27-7.34 (m, 6H), 7.40 (d, J=7.6 Hz, 1H), 7.51 (t, J=8.0 Hz, 1H), 7.76 (s, 1H), 8.40 (s, 1H).

Example 40

(Z)-tert-Butyl 4-((6-(4-((2,4-dioxothiazolidin-5-ylidene)methyl)-2-methoxyphenoxy)pyrimidin-4-yl)oxy)piperidine-1-carboxylate ¹HNMR: δ 1.48 (s, 9H), 1.73-1.78 (m, 2H), 1.97-2.02 (m, 2H), 3.26-3.33 (m, 2H), 3.71-3.80 (m, 2H), 3.83 (s, 3H), 5.29-5.33 (m, 1H), 6.31 (s, 1H), 7.05 (s, 1H), 7.11 (dd, J=8.4 & 2.0 Hz, 1H), 7.23 (d, J=8.4 Hz, 1H), 7.70 (s, 1H), 8.35 (s, 1H), 9.83 (s, 1H).

Example 41

(Z)-5-(4-((6-((1-(5-Ethylpyrimidin-2-yl)piperidin-4-yl)oxy)pyrimidin-4-yl)oxy)benzylidene)thiazolidine-2,4-dione ¹HNMR: δ 1.21 (t, J=7.61 Hz, 3H), 1.77-1.85 (m, 2H), 2.06-2.12 (m, 2H), 2.44-2.50 (m, 2H), 3.55-3.61 (m, 2H), 4.24-4.30 (m, 2H), 5.37-5.42 (m, 1H), 6.26 (s, 1H), 7.24-7.27 (m, 2H), 7.53-7.57 (m, 2H), 7.80 (s, 1H), 8.19 (s, 2H), 8.44 (s, 1H), 9.05 (s, 1H).

Example 42

(Z)-5-(3-((6-((1-(Pyrimidin-2-yl)piperidin-4-yl)oxy)pyrimidin-4-yl)oxy)benzylidene)thiazolidine-2,4-dione ¹HNMR (DMSO-d6): δ 1.60-1.68 (m, 2H), 2.02-2.06 (m, 2H), 3.47-3.54 (m, 2H), 4.22-4.28 (m, 2H), 5.33-5.39 (m, 1H), 6.46 (s, 1H), 6.62 (t, J=4.4 Hz, 1H), 7.32-7.34 (m, 1H), 7.44 (t, J=3.6 Hz, 1H), 7.49 (d, J=8.10 Hz, 1H), 7.60 (t, J=8.0 Hz, 1H), 7.80 (s, 1H), 8.36 (d, J=4.8 Hz, 2H), 8.48 (s, 1H), 12.66 (s, 1H).

Example 43

(Z)-5-(4-((6-((1-(Pyrimidin-2-yl)piperidin-4-yl)oxy)pyrimidin-4-yl)oxy)benzylidene)thiazolidine-2,4-dione ¹HNMR (DMSO-d6): δ 1.64-1.68 (m, 2H), 2.02-2.06 (m, 2H), 3.47-3.54 (m, 2H), 4.22-4.28 (m, 2H), 5.33-5.39 (m, 1H), 6.48 (s, 1H), 6.61 (t, J=4.8 Hz, 1H), 7.36 (d, J=8.4 Hz, 2H), 7.67 (d, J=8.40 Hz, 2H), 7.79 (s, 1H), 8.36 (d, J=4.8 Hz, 2H), 8.48 (s, 1H), 12.63 (s, 1H).

Example 44

(Z)-tert-Butyl 4-((6-(3-((2,4-dioxo-3-(2-oxopropyl)thiazolidin-5-ylidene)methyl)phenoxy)-5-methylpyrimidin-4-yl)oxy)piperidine-1-carboxylate ¹HNMR: δ 1.48 (s, 9H), 1.76-1.83 (m, 2H), 1.97-2.02 (m, 2H), 2.19 (s, 3H), 2.27 (s, 3H), 3.35-3.41 (m, 2H), 3.70-3.75 (m, 2H), 4.54 (s, 2H), 5.32-5.36 (m, 1H), 7.19-7.23 (m, 1H), 7.29 (d, J=3.6 Hz, 1H), 7.38 (d, J=7.6 Hz, 1H), 7.52 (t, J=8.10 Hz, 1H), 7.89 (s, 1H), 8.24 (s, 1H).

Example 45

(Z)-tert-Butyl 4-((6-(3-((3-(2-ethoxy-2-oxoethyl)-2,4-dioxothiazolidin-5-ylidene)methyl)phenoxy)-5-methylpyrimidin-4-yl)oxy)piperidine-1-carboxylate ¹HNMR: δ 1.29 (t, J=6.8 Hz, 3H), 1.48 (s, 9H), 1.76-1.83 (m, 2H), 1.97-2.02 (m, 2H), 2.19 (s, 3H), 3.35-3.41 (m, 2H), 3.71-3.76 (m, 2H), 4.24 (q, J=7.2 Hz, 2H), 4.47 (s, 2H), 5.32-5.36 (m, 1H), 7.20-7.22 (m, 1H), 7.29 (d, J=4.0 Hz, 1H), 7.38 (d, J=7.6 Hz, 1H), 7.52 (t, J=8.0 Hz, 1H), 7.91 (s, 1H), 8.24 (s, 1H).

Example 46

(Z)-tert-Butyl 4-((6-(4-((2,4-dioxo-3-(2-oxopropyl)thiazolidin-5-ylidene)methyl)phenoxy)pyrimidin-4-yl)oxy)piperidine-1-carboxylate ¹HNMR: δ 1.47 (s, 9H), 1.71-1.76 (m, 2H), 1.96-2.04 (m, 2H), 2.28 (s, 3H), 3.24-3.31 (m, 2H), 3.74-3.79 (m, 2H), 4.56 (s, 2H), 5.28-5.32 (m, 1H), 6.22 (s, 1H), 7.24-7.28 (m, 2H), 7.56-7.60 (m, 2H), 7.91 (s, 1H), 8.42 (s, 1H).

Example 47

(Z)-5-(3-((6-((1-(5-Chloropyrimidin-2-yl)piperidin-4-yl)oxy)-5-methylpyrimidin-4-yl)oxy)benzylidene)thiazolidine-2,4-dione ¹HNMR (DMSO-d6): δ 1.60-1.68 (m, 2H), 2.01-2.09 (m, 2H), 2.14 (s, 3H), 3.68-3.74 (m, 2H), 4.04-4.10 (m, 2H), 5.38-5.43 (m, 1H), 7.28-7.30 (m, 1H), 7.40-7.41 (t, J=3.6 Hz, 1H), 7.46 (d, J=8.0 Hz, 1H), 7.58 (t, J=8.0 Hz, 1H), 7.79 (s, 1H), 8.29 (s, 1H), 8.43 (s, 2H), 12.66 (s, 1H).

Example 48

(Z)-5-(3-((6-((1-(5-Bromopyridin-2-yl)piperidin-4-yl)oxy)-5-methylpyrimidin-4-yl)oxy)benzylidene)thiazolidine-2,4-dione $^1$HNMR: δ 1.85-1.93 (m, 2H), 2.07-2.15 (m, 2H), 2.19 (s, 3H), 3.47-3.53 (m, 2H), 3.85-3.91 (m, 2H), 5.39-5.45 (m, 1H), 6.61 (d, J=8.8 Hz, 1H), 7.19-7.22 (m, 1H), 7.27 (d, J=3.6 Hz, 1H), 7.36 (d, J=7.6 Hz, 1H), 7.50-7.55 (m, 2H), 7.80 (s, 1H), 8.20 (d, J=2.0 Hz, 1H), 8.25 (s, 1H).

Example 49

(3R,4S)-tert-Butyl 4-((6-(3-((Z)-(2,4-dioxothiazolidin-5-ylidene)methyl)phenoxy)-5-methylpyrimidin-4-yl)oxy)-3-fluoropiperidine-1-carboxylate $^1$HNMR (DMSO-d6): δ 1.41 (s, 9H), 1.85-1.90 (m, 2H), 2.14 (s, 3H), 3.01-3.20 (m, 1H), 3.29-3.33 (m, 1H), 3.85-3.95 (m, 1H), 4.05-4.15 (m, 1H), 4.92 (s, 1H), 5.36-5.43 (m, 1H), 7.28 (dd, J=7.2 & 1.6 Hz, 1H), 7.41 (d, J=1.6 Hz, 1H), 7.47 (d, J=8.0 Hz, 1H), 7.59 (t, J=7.6 Hz, 1H), 7.79 (s, 1H), 8.28 (s, 1H), 12.65 (s, 1H).

Example 50

(Z)-Benzyl 4-((6-(3-((2,4-dioxothiazolidin-5-ylidene)methyl)phenoxy)-5-methylpyrimidin-4-yl)oxy)piperidine-1-carboxylate $^1$HNMR: δ 1.83 (bs, 2H), 2.02 (bs, 2H), 2.19 (s, 3H), 3.47-3.53 (m, 2H), 3.77-3.83 (m, 2H), 5.16 (s, 2H), 5.34-5.40 (m, 1H), 7.18-7.21 (m, 1H), 7.26-7.27 (m, 1H), 7.31-7.38 (m, 6H), 7.51 (t, J=8.0 Hz, 1H), 7.80 (s, 1H), 8.23 (s, 1H), 9.01 (s, 1H).

Example 51

(Z)-Ethyl 4-((6-(3-((2,4-dioxothiazolidin-5-ylidene)methyl)phenoxy)pyrimidin-4-yl)oxy)piperidine-1-carboxylate $^1$HNMR: δ 1.27 (t, J=9.2 Hz, 3H), 1.72-1.80 (m, 2H), 1.98-2.04 (m, 2H), 3.33-3.39 (m, 2H), 3.80-3.83 (m, 2H), 4.14 (q, J=7.2 Hz, 2H), 5.30-5.35 (m, 1H), 6.21 (s, 1H), 7.21-7.24 (m, 1H), 7.28-7.29 (m, 1H), 7.39 (d, J=8.0 Hz, 1H), 7.53 (t, J=8.0 Hz, 1H), 7.81 (s, 1H), 8.42 (s, 1H), 8.77 (s, 1H).

Example 52

(Z)-Ethyl 4-((6-(4-((2,4-dioxothiazolidin-5-ylidene)methyl)phenoxy)pyrimidin-4-yl)oxy)piperidine-1-carboxylate $^1$HNMR: δ 1.27 (t, J=7.2 Hz, 3H), 1.73-1.80 (m, 2H), 1.98-2.03 (m, 2H), 3.32-3.39 (m, 2H), 3.80-3.83 (m, 2H), 4.15 (q, J=7.2 Hz, 2H), 5.30-5.36 (m, 1H), 6.25 (s, 1H), 7.24-7.26 (m, 2H), 7.55 (d, J=8.4 Hz, 2H), 7.80 (s, 1H), 8.42 (s, 1H).

Example 53C (Z)-Isobutyl 4-((6-(4-((2,4-dioxothiazolidin-5-ylidene)methyl)phenoxy)pyrimidin-4-yl)oxy)piperidine-1-carboxylate $^1$HNMR: δ 0.94 (d, J=6.8 Hz, 6H), 1.74-1.81 (m, 2H), 1.91-2.04 (m, 3H), 3.34-3.40 (m, 2H), 3.81-3.85 (m, 2H), 3.88 (d, J=6.4 Hz, 2H), 5.31-5.35 (m, 1H), 6.26 (s, 1H), 7.23-7.27 (m, 2H), 7.53-7.57 (m, 2H), 7.80 (s, 1H), 8.42 (s, 1H), 9.03 (s, 1H).

Example 54

(Z)-Isobutyl 4-((6-(3-((2,4-dioxothiazolidin-5-ylidene)methyl)phenoxy)pyrimidin-4-yl)oxy)piperidine-1-carboxylate $^1$HNMR: δ 0.94 (d, J=6.8 Hz, 6H), 1.72-1.80 (m, 2H), 1.89-2.04 (m, 3H), 3.34-3.40 (m, 2H), 3.79-3.84 (m, 2H), 3.88 (d, J=6.4 Hz, 2H), 5.30-5.36 (m, 1H), 6.21 (s, 1H), 7.21-7.28 (m, 2H), 7.39 (d, J=8.0 Hz, 1H), 7.53 (t, J=8.0 Hz, 1H), 7.82 (s, 1H), 8.42 (s, 1H), 8.61 (s, 1H).

Example 55

(2)-5-(3-((6-((1-(5-Ethylpyrimidin-2-ylpiperidin-4-yl)oxy)pyrimidin-4-yl)oxy)benzylidene)thiazolidine-2,4-ione $^1$HNMR: δ 1.19 (t, J=7.6 Hz, 3H), 1.76-1.85 (m, 2H), 2.06-2.50 (m, 2H), 2.47 (q, J=7.6 Hz, 2H), 3.54-3.61 (m, 2H), 4.24-4.30 (m, 2H), 5.38-5.42 (m, 1H), 6.21 (s, 1H), 7.16 (dd, J=7.2 & 2.4 Hz, 2H), 7.22-7.27 (m, 1H), 7.38 (d, J=8.0 Hz, 1H), 7.53 (t, J=8.0 Hz, 1H), 7.82 (s, 1H), 8.19 (s, 2H), 8.44 (s, 1H).

Example 56

(Z)-6-(4-((6-(3-((2,4-Dioxothiazolidin-5-ylidene)methyl)phenoxy)-5-methylpyrimidin-4-yl)oxy)piperidin-1-yl)nicotinonitrile $^1$HNMR (DMSO-d6): δ 1.78-1.85 (m, 2H), 2.02-2.07 (m, 2H), 2.14 (s, 3H), 3.65-3.71 (m, 2H), 3.97-4.03 (m, 2H), 5.40-5.44 (m, 1H), 7.01 (d, J=9.2 Hz, 1H), 7.24 (dd, J=7.6 & 1.6 Hz, 1H), 7.37 (d, J=1.6 Hz, 1H), 7.45 (d, J=8.0 Hz, 1H), 7.55 (t, J=8.0 Hz, 1H), 7.68 (s, 1H), 7.85 (dd, J=9.2 & 2.4, 1H), 8.28 (s, 1H), 8.49 (d, J=2.4 Hz, 1H).

Example 57

(Z)-tert-Butyl 4-((6-(3-((3-benzyl-2,4-dioxothiazolidin-5-ylidene)methyl)phenoxy)-5-methylpyrimidin-4-yl)oxy)piperidine-1-carboxylate $^1$HNMR: δ 1.48 (s, 9H), 1.74-1.82 (m, 2H), 1.96-2.01 (m, 2H), 2.18 (s, 3H), 3.35-3.41 (m, 2H), 3.70-3.76 (m, 2H), 4.89 (s, 2H), 5.32-3.36 (m, 1H), 7.17-7.20 (m, 1H), 7.25-7.28 (m, 1H), 7.30-7.43 (m, 5H), 7.44-7.51 (m, 1H), 7.87 (s, 1H), 8.23 (s, 1H).

Example 58

(Z)-tert-Butyl 4-((6-(3-((3-allyl-2,4-dioxothiazolidin-5-ylidene)methyl)phenoxy)-5-methylpyrimidin-4-yl)oxy)piperidine-1-carboxylate $^1$HNMR: δ 1.49 (s, 9H), 1.78-1.83 (m, 2H), 1.98-2.03 (m, 2H), 2.20 (s, 3H), 3.36-3.43 (m, 2H), 3.71-3.76 (m, 2H), 4.35-4.37 (m, 2H), 5.25-5.36 (m, 3H), 5.83-5.90 (m, 1H), 7.19-7.22 (m, 1H), 7.27-7.30 (m, 1H), 7.38 (d, J=7.6 Hz, 1H), 7.52 (t, J=7.6 Hz, 1H), 7.90 (s, 1H), 8.25 (s, 1H).

Example 59

(Z)-tert-Butyl 4-((6-(3-((3-(2-bromoethyl)-2,4-dioxothiazolidin-5-ylidene)methyl)phenoxy)-5-methylpyrimidin-4-yl)oxy)piperidine-1-carboxylate $^1$HNMR: δ 1.49 (s, 9H), 1.78-1.83 (m, 2H), 1.98-2.03 (m, 2H), 2.20 (s, 3H), 3.36-3.42 (m, 2H), 3.60 (t, J=6.4 Hz, 2H), 3.71-3.77 (m, 2H), 4.17 (t, J=6.8 Hz, 2H), 5.34-5.37 (m, 1H), 7.21-7.23 (m, 1H), 7.30 (t, J=2.4 Hz, 1H), 7.39 (d, J=8.0 Hz, 1H), 7.53 (t, J=8.0 Hz, 1H), 7.91 (s, 1H), 8.25 (s, 1H).

Example 60

(Z)-tert-Butyl-4-((6-(3-((3-ethyl-2,4-dioxothiazolidin-5-ylidene)methyl)phenoxy)-5-methylpyrimidin-4-yl)oxy)piperidine-1-carboxylate $^1$HNMR (DMSO-d6): δ 1.16 (t, J=5.2 Hz, 3H), 1.47 (s, 9H), 1.60-1.68 (m, 2H), 1.91-1.98 (m, 2H), 2.14 (s, 3H), 2.49-2.51 (m, 2H), 3.31-3.71 (m, 4H), 5.29-5.33 (m, 1H), 7.28-7.31 (m, 1H), 7.43 (t, J=2.0 Hz, 1H), 7.49 (d, J=8M Hz, 1H), 7.59 (t, J=8.0 Hz, 1H), 7.93 (s, 1H), 8.27 (s, 1H).

Example 61

(Z)-3-Ethyl-5-(3-((6-((1-(5-ethylpyrimidin-2-yl)piperidin-4-yl)oxy)-5-methylpyrimidin-4-yl)oxy)benzylidene)thiazolidine-2,4-dione $^1$HNMR: δ 1.21 (t, J=7.6 Hz, 3H), 1.28 (t, J=7.2 Hz, 3H), 1.85-1.91 (m, 2H), 2.06-2.12 (m, 2H), 2.20 (s, 3H), 2.49 (q, J=7.6 Hz, 2H), 3.69-3.74 (m, 2H), 3.83 (q, J=7.2 Hz, 2H), 4.17-4.23 (m, 2H), 5.43-5.47 (m, 1H), 7.19-7.26 (m, 1H), 7.30 (t, J=2.0 Hz, 1H), 7.38 (d, J=7.6 Hz, 1H), 7.51 (dd, J=8.0 & 4.8 Hz, 1H), 7.89 (s, 1H), 8.21 (dd, J=5.6 Hz, 2H), 8.27 (s, 1H).

Example 62

(Z)-5-(3-((6-((1-(5-Ethylpyrimidin-2-yl)piperidin-4-yl)oxy)-5-methylpyrimidin-4-yl)oxy)benzylidene)-3-(2-oxopropyl)thiazolidine-2,4-dione $^1$HNMR: δ 1.20 (t, J=7.6 Hz, 3H), 1.81-1.90 (m, 2H), 2.05-2.12 (m, 2H), 2.19 (s, 3H), 2.26 (s, 3H), 2.47 (q, J=7.6 Hz, 2H), 3.67-3.74 (m, 2H), 4.16-4.22 (m, 2H), 4.54 (s, 2H), 5.41-5.47 (m, 1H), 7.20-7.23 (m, 1H), 7.30 (t, J=2.0 Hz, 1H), 7.38 (d, J=8.0 Hz, 1H), 7.52 (t, J=8.0 Hz, 1H), 7.89 (s, 1H), 8.19 (s, 1H), 8.26 (s, 1H).

Example 63

(Z)-5-(3-((6-((1-(isopropylsulfonyl)piperidin-4-yl)oxy)-5-methylpyrimidin-4-yl)oxy)benzylidene)thiazolidine-2,4-dione $^1$HNMR (DMSO-d6): δ 1.23 (d, J=6.8 Hz, 6H), 1.72-1.80 (m, 2H), 2.00-2.05 (m, 2H), 2.15 (s, 3H), 3.32-3.39 (m, 3H), 3.46-3.52 (m, 2H), 5.30-5.34 (m, 1H), 7.28 (dd, J=8.0 & 1.6 Hz, 1H), 7.40 (s, 1H), 7.46 (d, J=8.0 Hz, 1H), 7.58 (t, J=8.0 Hz, 1H), 7.79 (s, 1H), 8.27 (s, 1H), 12.65 (s, 1H).

Example 64

(Z)-5-(3-((6-((1-acetylpiperidin-4-yl)oxy)pyrimidin-4-yl)oxy)benzylidene)thiazolidine-2,4-dione $^1$HNMR (DMSO-d6): δ 1.50-1.58 (m, 1H), 1.62-1.71 (m, 1H), 1.93-1.96 (m, 2H), 2.02 (s, 3H), 3.17-3.23 (m, 1H), 3.33-3.37 (m, 1H), 3.67-3.70 (m, 1H), 3.86-3.90 (m, 1H), 5.26-5.75 (m, 1H), 6.46 (s, 1H), 7.31-7.33 (m, 1H), 7.44 (s, 1H), 7.49 (d, J=8.0 Hz, 1H), 7.61 (t, J=7.6 Hz, 1H), 7.80 (s, 1H), 8.46 (s, 1H), 12.67 (s, NH).

Example 65

(Z)-5-(4-((6-((1-acetylpiperidin-4-yl)oxy)pyrimidin-4-yl)oxy)benzylidene)thiazolidine-2,4-dione $^1$HNMR (DMSO-d6): δ 1.66-1.70 (m, 1H), 1.70-1.78 (m, 1H), 1.97-2.01 (m, 2H), 2.02 (s, 3H), 3.16-3.23 (m, 1H), 3.32-3.37 (m, 1H), 3.67-3.70 (m, 1H), 3.87-3.90 (m, 1H), 5.27-5.31 (m, 1H), 6.48 (s, 1H), 7.36 (d, J=6.8 Hz, 2H), 7.68 (d, J=8.8 Hz, 2H), 7.83 (s, 1H), 8.47 (s, 1H), 12.64 (s, NH).

Example 66

(Z)-5-(3-((6-((1-(3-isopropyl-1,2,4-oxadiazol-5-yl)piperidin-4-yl)oxy)pyrimidin-4-yl)oxy)benzylidene)thiazolidine-2,4-dione $^1$HNMR (CDCl$_3$): δ 1.30 (d, J=7.2 Hz, 6H), 1.88-1.96 (m, 2H), 2.07-2.14 (m, 2H), 2.86-2.93 (m, 1H), 3.56-3.62 (m, 2H), 3.85-3.91 (m, 2H), 5.38-5.43 (m, 1H), 6.23 (s, 1H), 7.21-7.24 (m, 1H), 7.29 (t, J=2.0 Hz, 1H), 7.39 (d, J=7.6 Hz, 1H), 7.54 (t, J=8.0 Hz, 1H), 7.82 (s, 1H), 8.43 (s, 1H).

Example 67

(Z)-5-(3-((6-((1-(3-isopropyl-1,2,4-oxadiazol-5-yl)piperidin-4-yl)oxy)-5-ethylpyrimidin-4-yl)oxy)benzylidene)-3-methylthiazolidine-2,4-dione $^1$HNMR (DMSO-d6): δ 1.19 (d, J=6.8 Hz, 6H), 1.80-1.84 (m, 2H), 2.04-2.10 (m, 2H), 2.15 (s, 3H), 2.81-2.84 (m, 1H), 3.11 (s, 3H), 3.56-3.61 (m, 2H), 3.73-3.78 (m, 2H), 5.37-5.39 (m, 1H), 7.29-7.32 (m, 1H), 7.44 (t, J=1.6 Hz, 1H), 7.49 (d, J=8.0 Hz, 1H), 7.60 (t, J=8.0 Hz, 1H), 7.93 (s, 1H), 8.29 (s, 1H).

Example 68

(Z)-5-(3-((6-((1-(3-isopropyl-1,2,4-oxadiazol-5-yl)piperidin-4-yl)oxy)-5-ethylpyrimidin-4-yl)oxy)benzylidene)-3-(2-oxopropyl)thiazolidine-2,4-dione $^1$HNMR (CDCl$_3$): δ 1.31 (d, J=6.8 Hz, 6H), 1.92-2.00 (m, 2H), 2.08-2.15 (m, 2H), 2.20 (s, 3H), 2.27 (s, 3H), 2.87-2.94

(m, 1H), 3.62-3.68 (m, 2H), 3.83-3.89 (m, 2H), 4.55 (s, 2H), 5.30-5.45 (m, 1H), 7.21 (dd, J=8.0 & 1.6 Hz, 1H), 7.29 (s, 1H), 7.38 (d, J=8.0 Hz, 1H), 7.52 (t, J=8.0 Hz, 1H), 7.90 (s, 1H), 8.25 (s, 1H).

Example 69

(Z)-3-isopropyl-5-(3-((6-((1-(3-isopropyl-1,2,4-oxadiazol-5-yl)piperidin-4-yl)oxy)-5-methylpyrimidin-4-yl)oxy)benzylidene)thiazolidine-2,4-dione $^1$HNMR (CDCl$_3$): δ 1.30 (d, J=6.8 Hz, 6H), 1.48 (d, J=7.2 Hz, 6H), 1.93-2.00 (m, 2H), 2.07-2.14 (m, 2H), 2.20 (s, 3H), 2.87-2.94 (m, 1H), 3.62-3.68 (m, 2H), 3.84-3.89 (m, 2H), 4.63-4.70 (m, 2H), 5.30-5.45 (m, 1H), 7.17-7.20 (m, 1H), 7.37 (d, J=8.0 Hz, 1H), 7.49-7.53 (dd, J=8.0 & 4.4 Hz, 1H), 7.82 (s, 1H), 8.25 (s, 1H).

Example 70

(Z)-6-(4-((6-(3-((2,4-dioxothiazolidin-5-yl idene)methyl)phenoxy)pyrimidin-4-yl)oxy)piperidin-1-yl)nicotinonitrile $^1$HNMR (DMSO-d6): δ 1.70-1.72 (m, 2H), 2.03-2.08 (m, 2H), 3.50-3.56 (m, 2H), 4.07-4.11 (m, 2H), 5.35-5.39 (m, 1H), 6.46 (s, 1H), 6.99 (d, J=9.2 Hz, 1H), 7.31-7.33 (m, 1H), 7.44 (t, J=2.0 Hz, 1H), 7.49 (d, J=7.6 Hz, 1H), 7.61 (t, J=8.4 Hz, 1H), 7.80 (s, 1H), 7.85 (dd, J=9.2 & 2.4 Hz, 1H), 8.48-8.49 (m, 2H), 12.67 (s, 1H, NH).

Example 71

(Z)-5-(3-((6-((1-(methylsulfonyl)piperidin-4-yl)oxy)pyrimidin-4-yl)oxy)benzyl idene)thiazolidine-2,4-dione $^1$HNMR (CDCl$_3$): δ 1.75-1.85 (m, 2H), 2.05-2.09 (m, 2H), 2.90 (s, 3H), 3.10-3.16 (m, 2H), 3.36-3.39 (m, 2H), 5.20-5.26 (m, 1H), 6.46 (s, 1H), 7.32 (dd, J=8.0 & 1.6 Hz, 1H), 7.44 (t, J=1.6 Hz, 1H), 7.49 (d, J=8.0 Hz, 1H), 7.61 (t, J=7.6 Hz, 1H), 7.80 (s, 1H), 8.47 (s, 1H), 12.67 (s, 1H, NH)

Example 72

(Z)-5-(3-((6-((1-(5-chloropyrimidin-2-yl)piperidin-4-yl)oxy)pyrimidin-4-yl)oxy)benzylidene)thiazolidine-2,4-dione $^1$HNMR (DMSO-d6): δ 1.62-1.69 (m, 2H), 2.03-2.05 (m, 2H), 3.54 (t, J=9.6 Hz, 2H), 4.17-4.20 (m, 2H), 5.35-5.36 (m, 1H), 6.46 (s, 1H), 7.32 (d, J=7.6 Hz, 1H), 7.44 (s, 1H), 7.49 (d, J=7.6 Hz, 1H), 7.61 (t, J=8.0 Hz, 1H), 7.80 (s, 1H), 8.42 (s, 2H), 8.47 (s, 1H), 12.67 (s, 1H, NH).

Example 73

(Z)-5-(4-((6-((1-(5-chloropyrimidin-2-yl)piperidin-4-yl)oxy)pyrimidin-4-yl)oxy)benzylidene)thiazolidine-2,4-dione $^1$HNMR (DMSO-d6): δ 1.63-1.70 (m, 2H), 2.02-2.05 (m, 2H), 3.51-3.56 (m, 2H), 4.17-4.20 (m, 2H), 5.34-5.38 (m, 1H), 6.49 (s, 1H), 7.37 (d, J=8.4 Hz, 2H), 6.68 (d, J=8.8 Hz, 2H), 7.83 (s, 1H), 8.42 (s, 2H), 8.48 (s, 1H), 12.64 (s, 1H, NH).

Example 74

(Z)-3-(methylsulfonyl)-5-(4-((6-((1-(methylsulfonyl)piperidin-4-yl)oxy)pyrimidin-4-yl)oxy)benzylidene)thiazolidine-2,4-dione $^1$HNMR (DMSO-d6): δ 1.76-1.83 (m, 2H), 2.04-2.09 (m, 2H), 2.90 (s, 3H), 3.10-3.16 (m, 2H), 3.35-3.40 (m, 2H), 3.66 (s, 3H), 5.22-5.25 (m, 1H), 6.51 (s, 1H), 7.40 (dd, J=6.8 & 1.6 Hz, 2H), 7.72 (d, J=8.4 Hz, 2H), 8.02 (s, 1H), 8.48 (s, 1H).

Example 75

(Z)-5-(4-((6-((1-(5-bromopyridin-2-yl)piperidin-4-yl)oxy)pyrimidin-4-yl)oxy)benzylidene)thiazolidine-2,4-dione $^1$HNMR (DMSO-d6): δ 1.61-1.70 (m, 2H), 2.03-2.08 (m, 2H), 3.30-3.37 (m, 2H), 3.93-3.99 (m, 2H), 5.30-5.36 (m, 1H), 6.48 (s, 1H), 6.89 (d, J=9.2 Hz, 1H), 7.36 (dd, J=6.8 & 2.0 Hz, 2H), 7.66-7.69 (m, 3H), 7.82 (s, 1H), 8.16 (d, J=2.4 Hz, 1H), 8.48 (s, 1H), 12.64 (s, 1H).

Example 76

D232-TBR-010

(Z)-5-(3-((6-((1-(5-bromopyridin-2-yl)piperidin-4-yl)oxy)pyrimidin-4-yl)oxy)benzylidene)thiazolidine-2,4-dione $^1$HNMR (DMSO-d6): δ 1.69-1.70 (m, 2H), 2.02-2.05 (m, 2H), 3.32-3.37 (m, 2H), 3.93-3.99 (m, 2H), 5.30-5.36 (m, 1H), 6.45 (s, 1H), 6.89 (d, J=9.2 Hz, 1H), 7.31 (dd, J=7.6 & 1.6 Hz, 1H), 7.43 (t, J=2.0 Hz, 1H), 7.49 (d, J=7.6 Hz, 1H), 7.60 (t, J=8.0 Hz, 1H), 7.67 (dd, J=10.8 & 2.4 Hz, 1H), 7.74 (s, 1H), 8.46 (d, J=2.8 Hz, 1H), 8.47 (s, 1H), 12.75 (s, 1H).

The novel compounds of the present invention can be formulated into suitable pharmaceutically acceptable compositions by combining with suitable excipients by techniques and processes and concentrations as are well known.

The compounds of formula (I) or pharmaceutical compositions containing them are useful as ligands of the GPR-119 receptor suitable for humans and other warm blooded animals, and may be administered either by oral, topical or parenteral administration. The quantity of active component, that is, the compounds of formula (I) according to this invention, in the pharmaceutical composition and unit dosage form thereof may be varied or adjusted widely depending upon several factors such as the particular application method, the potency of the particular compound and the desired concentration.

Biological Activity:

The biological activity of the compounds of the present invention were tested in the following in vitro and in vivo models mentioned here.

cAMP Assay:

A stable cell line expressing recombinant human GPR 119 receptor was established and used to investigate the efficacy of the compounds of the invention based on the intracellular levels of cyclic AMP (cAMP) using commercially available cAMP kits. Compounds of the invention produced a concentration dependent increase in cAMP level and the data was provided in Table 1 and Table 2.

TABLE 1

Fold increase in cyclic AMP with respective to DMSO.

| Example DMSO | 1 | 10 nM | 100 nM | 1 uM |
|---|---|---|---|---|
| 18 | | 1.50 | 2.57 | 4.03 |
| 10 | | 1.14 | 2.30 | 5.06 |
| 24 | | 1.07 | 1.11 | 2.27 |
| 3 | | 0.64 | 0.88 | 2.02 |
| 19 | | 1.31 | 1.92 | 4.24 |
| 21 | | 0.92 | 1.06 | 2.35 |
| 20 | | 0.59 | 2.02 | 2.39 |
| 23 | | 0.90 | 1.29 | 1.11 |
| 22 | | 0.95 | 1.82 | 1.66 |
| 13 | | 0.61 | 0.63 | 1.42 |
| 7 | | 0.79 | 1.32 | 2.24 |
| 1 | | 0.90 | 2.27 | 3.96 |
| 17 | | 0.84 | 1.06 | 2.57 |
| 16 | | 1.91 | 2.54 | 3.17 |
| 8 | | 0.52 | 0.85 | 1.67 |
| 15 | | 1.72 | 2.19 | 3.28 |
| 14 | | 1.40 | 2.40 | 6.61 |
| 12 | | 2.22 | 4.47 | 7.00 |
| 9 | | 2.54 | 4.86 | 6.57 |
| 25 | | 3.32 | 5.81 | 1.39 |
| 26 | | 4.02 | 7.17 | 9.34 |
| 50 | | 1.73 | 4.66 | 5.74 |
| 27 | | 1.38 | 2.89 | 4.79 |
| 28 | | 1.32 | 2.86 | 4.56 |
| 30 | | 2.29 | 3.59 | 7.4 |
| 29 | | 2.09 | 3.66 | 8.17 |
| 4 | | 4.52 | 4.95 | 7.17 |
| 54 | | 1.31 | 2.28 | 4.11 |
| 53 | | 0.99 | 1.79 | 3.59 |
| 39 | | 0.85 | 1.38 | 2.20 |
| 40 | | 0.87 | 1.21 | 1.66 |
| 11 | | 1.00 | 1.38 | 2.51 |
| 2 | | 5.90 | 8.00 | 12.56 |
| 31 | | 1.06 | 2.27 | 3.66 |
| 32 | | 0.77 | 0.94 | 1.45 |
| 33 | | 0.83 | 1.36 | 2.72 |
| 34 | | 0.73 | 1.09 | 2.22 |
| 35 | | 0.56 | 0.57 | 0.96 |
| 36 | | 0.80 | 1.38 | 2.19 |
| 52 | | 1.15 | 1.94 | 3.36 |
| 51 | | 0.79 | 1.25 | 2.81 |
| 37 | | 0.97 | 1.47 | 2.07 |
| 38 | | 0.34 | 0.67 | 1.64 |
| 55 | | 1.18 | 2.86 | 4.77 |
| 41 | | 1.00 | 1.58 | 3.53 |
| 42 | | 0.65 | 1.27 | 3.10 |
| 43 | | 0.94 | 1.27 | 1.98 |
| 46 | | 1.58 | 1.89 | 5.45 |
| 45 | | 1.05 | 1.33 | 2.88 |

TABLE 2

$EC_{50}$ in cAMP assay.

| Example | $EC_{50}$ nM |
|---|---|
| 1 | 88 |
| 7 | 124 |
| 9 | 43 |
| 12 | 130 |
| 66 | 71 |

In Vivo Efficacy Studies:

Oral Glucose Tolerance Tests (OGTT) in C57/13L6 mice:

C57/BL6 mice of 6-8 week age are used for this experiment. Animals are grouped based on non-fasting serum glucose levels and kept on fasting for overnight (day before OGTT). On the experiment day, each animal receive a single dose of vehicle/test compounds (30 mg/kg) administered orally, 30 min post dosing animals are bled for basal glucose level estimation and at the same time glucose load (3 gm/kg) will be administered per orally. Blood is collected at time points corresponding to 20, 40, 60 and 120 min after glucose load administration. Serum is separated for determination of glucose levels and change in area under curve for glucose is calculated and provided in Table 3 as % to reduction in AUC.

TABLE 3

| Example | % reduction in AUC at 50 mg/kg |
|---|---|
| 1 | 35.0 |
| 2 | 13.0 |
| 7 | 29.0 |
| 9 | 32.4 |
| 12 | 23.4 |
| 66 | 41.1 |

Oral Glucose Tolerance Tests (OGTT) in db/db mice:

db/db mice of 5-7 week age are used for this experiment. Animals were kept on fasting and are grouped based on fasting serum glucose levels and after grouping OGTT was performed. Each animal receive a single dose of vehicle/test compounds (50 mg/kg) administered orally, 30 min post dosing animals are bled for basal glucose level estimation and at the same time glucose load (2 g/kg) will be administered per orally. Blood is collected at time points corresponding to 30, 60 and 120 min after glucose load administration. Serum is separated for determination of glucose levels and change in area under curve for glucose and glucose excursion is calculated from Vehicle control with glucose load Vs water control group without glucose load and provided in Table 4 as % reduction in AUC glucose excursion Vs Vehicle control is calculated.

TABLE 4

| Example | % reduction in AUC at 50 mg/kg |
|---|---|
| 1 | 56.2 |
| 2 | 47.3 |
| 7 | 22.4 |
| 9 | 69.1 |
| 12 | 66.7 |

Thus, the compounds of the present invention are selective to the GPR-119 receptor and shows potential to reduce food intake and thereby has potential to help control/reduce obesity. Additionally, they have potential glucose reducing effects in various degrees. Thus, these compounds may be useful as potential treatments of diabetes &/or obesity.

The novel compounds of the present invention (I) may be formulated into suitable pharmaceutically acceptable compositions by combining with suitable excipients by techniques and processes and concentrations as are well known.

The compounds of formula (I) or pharmaceutical compositions containing them are suitable for humans and other warm blooded animals, and may be administered either by oral, topical or parenteral administration for the treatment of various disease conditions associated with dyslipidemia, obesity etc.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

We claim:
1. A compound of formula (I),

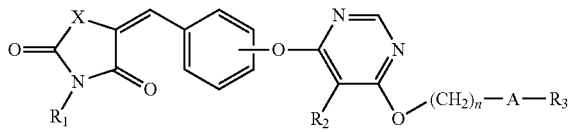

its tautomeric form, its stereoisomer, and pharmaceutically acceptable salt thereof
wherein
R$_1$ represents H or an optionally substituted group selected from a member of the group consisting of linear or branched (C$_1$-C$_6$)-alkyl, haloalkyl, (C$_1$-C$_6$)alkenyl, cycloalkyl, cycloalkylalkyl, heterocyclyl, heterocyclylalkyl, aryl, aralkyl, heteroaryl, heteroarylalkyl, alkylsulfonyl, and arylsulfonyl groups, or a group represented by (CH$_2$)$_m$CO$_2$R$_4$, (CH$_2$)$_m$COR$_4$ or (CH$_2$)$_m$CONH$_2$ wherein each R$_4$ independently represents H or a group selected from a member of the group consisting of linear or branched (C$_1$-C$_6$)alkyl, cycloalkyl, aryl, heterocyclyl and heteroaryl;
and m is an integer of 0 to 3;
R$_2$ represents H, cyano, nitro, formyl, linear or branched (C$_1$-C$_6$) alkyl, or (C$_1$-C$_6$) alkoxyl;
R$_3$ represents an optionally substituted group selected from a member of the group consisting of linear or branched (C$_1$-C$_6$)alkyl, aryl, aralkyl, cycloalkyl, cycloalkylalkyl, heterocyclyl, heterocyclylalkyl, heteroaryl, and heteroaralkyl or a group represented by C(O)OR$_5$, C(O)R$_5$, and SO$_2$R$_5$ wherein each R$_5$ independently represents H or an optionally substituted group selected from a member of the group consisting of linear or branched (C$_1$-C$_6$) alkyl, aryl, aralkyl, cycloalkyl, cycloalkylalkyl, heterocyclyl, hererocyclylalkyl, heteroaryl, and heteroaralkyl groups; n represents an integer from 0 to 3; and
"A" represents

wherein p represents an integer from 1 to 3; and X represents O or S.

2. The compound of claim 1
wherein R$_1$ is selected from a member of the group consisting of linear or branched (C$_1$-C$_6$) alkyl, haloalkyl, (C$_1$-C$_6$)alkenyl, cycloalkyl, aralkyl alkylsulfonyl, and arylsulfonyl groups, or a group represented by (CH$_2$)$_m$CO$_2$R$_4$, (CH$_2$)$_m$COR$_4$ or (CH$_2$)$_m$CONH$_2$ wherein each R$_4$ independently represents H or a group selected from a member of the group consisting of linear or branched (C$_1$-C$_6$)alkyl, cycloalkyl, aryl, heterocyclyl and heteroaryl; and m=is an integer from 0 to 3.

3. The compound of claim 1 wherein R$_1$ is selected from a member of the group consisting of linear or branched (C$_1$-C$_6$) alkyl, haloalkyl, (C$_1$-C$_6$) alkenyl, aralkyl alkylsulfonyl, and arylsulfonyl groups or a group represented by (CH$_2$)$_m$CO$_2$R$_4$, (CH$_2$)$_m$COR$_4$ or (CH$_2$)$_m$CONH$_2$ wherein each R$_4$ independently represents a group selected from a member of the group consisting of linear or branched (C$_1$-C$_6$)-alkyl and aryl groups, m=is an integer from 0 to 3.

4. The compound of claim 1 wherein R$_2$ is selected from a member of the group consisting of H, nitro, linear or branched (C$_1$-C$_6$)-alkyl, and (C$_1$-C$_6$) alkoxyl groups.

5. The compound of claim 1 wherein each of R$_1$, R$_3$, R$_4$ and R$_5$ are independently hydroxyl, oxo, halo, thio, nitro, amino, cyano, formyl, or a substituted or unsubstituted group selected from a member of the group consisting of amidino, alkyl, haloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid, ester, amide, carbonylamino, hydroxyalkyl, aminoalkyl, alkoxyalkyl, aryloxyalkyl, aralkoxyalkyl, alkylthio, thioalkyl, arylthio, alkylsulfonylamino, alkylsulfonyloxy, alkoxycarbonylamino, aryloxycarbonylamino, aralkyloxycarbonylamino, aminocarbonylamino, alkylaminocarbonylamino, alkoxyamino, hydroxylamino, sulfenyl derivatives, sulfonyl derivatives, and sulfonic acid.

6. The compound of claim 1 selected from a member of the group consisting of
(Z)-tert-Butyl 4-((6-(4-((2,4-dioxothiazolidin-5-ylidene)methyl)phenoxy)-5-methylpyrimidin-4-yl)oxy)piperidine-1-carboxylate;
(Z)-tert-Butyl-4-((6-(4-((3-(2-ethoxy-2-oxoethyl)-2,4-dioxothiazolidin-5-ylidene)methyl)phenoxy)-5-methylpyrimidin-4-yl)oxy)piperidine-1-carboxylate;
(Z)-5-(4-((6-((1-(5-Ethylpyrimidin-2-yl)piperidin-4-yl)oxy)-5-methylpyrimidin-4-yl)oxy)benzylidene)-3-(methylsulfonyl)thiazolidine-2,4-dione;
(Z)-Ethyl-4-((5-methyl-6-(3-((3-methyl-2,4-dioxothiazolidin-5-ylidene)methyl)phenoxy)pyrimidin-4-yl)oxy)piperidine-1-carboxylate;
(Z)-5-(3-((5-Methyl-6-((1-(methylsulfonyl)piperidin-4-yl)oxy)pyrimidin-4-yl)oxy)benzylidene)thiazolidine-2,4-dione;
(Z)-5-(3-((6-((1-acetylpiperidin-4-yl)oxy)-5-methylpyrimidin-4-yl)oxy)benzylidene)thiazolidine-2,4-dione;
(Z)-5-(4-((6-((1-(3-iso-Propyl-1,2,4-oxadiazol-5-yl)piperidin-4-yl)oxy)-5-methylpyrimidin-4-yl)oxy)benzylidene)thiazolidine-2,4-dione;
(Z)-tert-Butyl 4-((6-(4-((2,4-dioxothiazolidin-5-ylidene)methyl)-2-methoxyphenoxy)-5-methylpyrimidin-4-yl)oxy)piperidine-1-carboxylate;
(Z)-tert-Butyl 4-((6-(3-((2,4-dioxothiazolidin-5-ylidene)methyl)phenoxy)-5-methylpyrimidin-4-yl)oxy)piperidine-1-carboxylate;
(Z)-5-(4-((6-((1-(3-iso-Propyl-1,2,4-oxadiazol-5-yl)piperidin-4-yl)oxy)pyrimidin-4-yl)oxy)benzylidene)thiazolidine-2,4-dione;
(Z)-Methyl 4-((6-(4-((2,4-dioxothiazolidin-5-ylidene)methyl)phenoxy)-5-methylpyrimidin-4-yl)oxy)piperidine-1-carboxylate;
(Z)-tert-Butyl 4-((6-(4-((2,4-dioxothiazolidin-5-ylidene)methyl)phenoxy)pyrimidin-4-yl)oxy)piperidine-1-carboxylate;
(Z)-Benzyl 4-((6-(4-((2,4-dioxothiazolidin-5-ylidene)methyl)phenoxy)-5-methylpyrimidin-4-yl)oxy)piperidine-1-carboxylate;

(Z)-Ethyl 4-((6-(4-((2,4-dioxothiazolidin-5-ylidene)methyl)phenoxy)-5-methylpyrimidin-4-yl)oxy)piperidine-1-carboxylate;

(Z)-iso-Butyl 4-((6-(4-((2,4-dioxothiazolidin-5-ylidene)methyl)phenoxy)-5-methylpyrimidin-4-yl)oxy)piperidine-1-carboxylate;

(Z)-iso-Propyl 4-((6-(4-((2,4-dioxothiazolidin-5-ylidene)methyl)phenoxy)-5-methylpyrimidin-4-yl)oxy)piperidine-1-carboxylate;

(Z)-5-(4-((5-Methyl-6-((1-(pyrimidin-2-yl)piperidin-4-yl)oxy)pyrimidin-4-yl)oxy)benzylidene)thiazolidine-2,4-dione;

(Z)-tert-Butyl 2-(((6-(4-((2,4-dioxothiazolidin-5-ylidene)methyl)phenoxy)-5-methylpyrimidin-4-yl)oxy)methyl)pyrrolidine-1-carboxylate;

(Z)-tert-Butyl 4-((6-(3-((2,4-dioxothiazolidin-5-ylidene)methyl)phenoxy)pyrimidin-4-yl)oxy)piperidine-1-carboxylate;

(Z)-Ethyl 4-((6-(3-((2,4-dioxothiazolidin-5-ylidene)methyl)phenoxy)-5-methylpyrimidin-4-yl)oxy)piperidine-1-carboxylate;

(Z)-Methyl 4-((6-(3-((2,4-dioxothiazolidin-5-ylidene)methyl)phenoxy)-5-methylpyrimidin-4-yl)oxy)piperidine-1-carboxylate;

(Z)-iso-Butyl 4-((6-(3-((2,4-dioxothiazolidin-5-ylidene)methyl)phenoxy)-5-methylpyrimidin-4-yl)oxy)piperidine-1-carboxylate;

(Z)-tert-Butyl 2-(((6-(3-((2,4-dioxothiazolidin-5-ylidene)methyl)phenoxy)-5-methylpyrimidin-4-yl)oxy)methyl)pyrrolidine-1-carboxylate;

(Z)-tert-Butyl-4-((6-(4-((3-(methylsulfonyl)-2,4-dioxothiazolidin-5-ylidene)methyl)phenoxy)pyrimidin-4-yl)oxy)piperidine-1-carboxylate;

(Z)-5-(3-((6-((1-(3-Isopropyl-1,2,4-oxadiazol-5-yl)piperidin-4-yl)oxy)-5-methylpyrimidin-4-yl)oxy)benzylidene)thiazolidine-2,4-dione;

(Z)-5-(3-((6-((1-(5-Ethylpyrimidin-2-yl)piperidin-4-yl)oxy)-5-methylpyrimidin-4-yl)oxy)benzylidene)thiazolidine-2,4-dione;

(Z)-5-(3-((6-((1-Benzylpiperidin-4-yl)oxy)-5-methylpyrimidin-4-yl)oxy)benzylidene)thiazolidine-2,4-dione;

(Z)-5-(3-((5-Methyl-6-((1-(pyrimidin-2-yl)piperidin-4-yl)oxy)pyrimidin-4-yl)oxy)benzylidene)thiazolidine-2,4-dione;

(Z)-Benzyl-4-((6-(3-((2,4-dioxothiazolidin-5-ylidene)methyl)phenoxy)pyrimidin-4-yl)oxy)piperidine-1-carboxylate;

(Z)-Benzyl-4-((6-(4-((2,4-dioxothiazolidin-5-ylidene)methyl)phenoxy)pyrimidin-4-yl)oxy)piperidine-1-carboxylate;

(Z)-tert-Butyl 4-((6-(4-((3-ethyl-2,4-dioxothiazolidin-5-ylidene)methyl)phenoxy)pyrimidin-4-yl)oxy)piperidine-1-carboxylate;

(Z)-Methyl 4-((6-(3-((3-isopropyl-2,4-dioxothiazolidin-5-ylidene)methyl)phenoxy)-5-methylpyrimidin-4-yl)oxy)piperidine-1-carboxylate;

(Z)-Isobutyl 4-((6-((3-((2,4-dioxothiazolidin-5-ylidene)methyl)phenoxy)pyrimidin-4-yl)oxy)piperidine-1-carboxylate;

(Z)-Isobutyl 4-((6-(4-((2,4-dioxothiazolidin-5-ylidene)methyl)phenoxy)pyrimidin-4-yl)oxy)piperidine-1-carboxylate;

(Z)-Methyl-4-((6-(4-((2,4-dioxothiazolidin-5-ylidene)methyl)phenoxy)pyrimidin-4-yl)oxy)piperidine-1-carboxylate;

(Z)-Methyl-4-((6-(3-((2,4-dioxothiazolidin-5-ylidene)methyl)phenoxy)pyrimidin-4-yl)oxy)piperidine-1-carboxylate;

(Z)-5-(4-((6-((1-Benzylpiperidin-4-yl)oxy)pyrimidin-4-yl)oxy)benzylidene)thiazolidine-2,4-dione;

(Z)-5-(4-((6-((1-Benzylpiperidin-4-yl)oxy)-5-methylpyrimidin-4-yl)oxy)benzylidene)thiazolidine-2,4-dione;

(Z)-5-(3-((6-((1-Benzylpiperidin-4-yl)oxy)pyrimidin-4-yl)oxy)benzylidene)thiazolidine-2,4-dione;

(Z)-tert-Butyl 4-((6-(4-((2,4-dioxothiazolidin-5-ylidene)methyl)-2-methoxyphenoxy)pyrimidin-4-yl)oxy)piperidine-1-carboxylate;

(Z)-5-(4-((6-((1-(5-Ethylpyrimidin-2-yl)piperidin-4-yl)oxy)pyrimidin-4-yl)oxy)benzylidene)thiazolidine-2,4-dione;

(Z)-5-(3-((6-((1-(Pyrimidin-2-yl)piperidin-4-yl)oxy)pyrimidin-4-yl)oxy)benzylidene)thiazolidine-2,4-dione;

(Z)-5-(4-((6-((1-(Pyrimidin-2-yl)piperidin-4-yl)oxy)pyrimidin-4-yl)oxy)benzylidene)thiazolidine-2,4-dione;

(Z)-tert-Butyl 4-((6-(3-((2,4-dioxo-3-(2-oxopropyl)thiazolidin-5-ylidene)methyl)phenoxy)-5-methylpyrimidin-4-yl)oxy)piperidine-1-carboxylate;

(Z)-tert-Butyl-4-((6-(3-((3-(2-ethoxy-2-oxoethyl)-2,4-dioxothiazolidin-5-ylidene)methyl)phenoxy)-5-methylpyrimidin-4-yl)oxy)piperidine-1-carboxylate;

(Z)-tert-Butyl-4-((6-(4-((2,4-dioxo-3-(2-oxopropyl)thiazolidin-5-ylidene)methyl)phenoxy)pyrimidin-4-yl)oxy)piperidine-1-carboxylate;

(Z)-5-(3-((6-((1-(5-Chloropyrimidin-2-yl)piperidin-4-yl)oxy)-5-methylpyrimidin-4-yl)oxy)benzylidene)thiazolidine-2,4-dione;

(Z)-5-(3-((6-((1-(5-Bromopyridin-2-yl)piperidin-4-yl)oxy)-5-methylpyrimidin-4-yl)oxy)benzylidene)thiazolidine-2,4-dione;

(3R,4S)-tert-Butyl 4-((6-(3-((Z)-(2,4-dioxothiazolidin-5-ylidene)methyl)phenoxy)-5-methylpyrimidin-4-yl)oxy)-3-fluoropiperidine-1-carboxylate;

(Z)-Benzyl 4-((6-(3-((2,4-dioxothiazolidin-5-ylidene)methyl)phenoxy)-5-methylpyrimidin-4-yl)oxy)piperidine-1-carboxylate;

(Z)-Ethyl-4-((6-(3-((2,4-dioxothiazolidin-5-ylidene)methyl)phenoxy)pyrimidin-4-yl)oxy)piperidine-1-carboxylate;

(Z)-Ethyl-4-((6-(4-((2,4-dioxothiazolidin-5-ylidene)methyl)phenoxy)pyrimidin-4-yl)oxy)piperidine-1-carboxylate;

(Z)-Isobutyl-4-((6-(4-((2,4-dioxothiazolidin-5-ylidene)methyl)phenoxy)pyrimidin-4-yl)oxy)piperidine-1-carboxylate;

(Z)-Isobutyl 4-((6-(3-((2,4-dioxothiazolidin-5-ylidene)methyl)phenoxy)pyrimidin-4-yl)oxy)piperidine-1-carboxylate;

(Z)-5-(3-((6-((1-(5-Ethylpyrimidin-2-yl)piperidin-4-yl)oxy)pyrimidin-4-yl)oxy)benzylidene)thiazolidine-2,4-ione;

(Z)-6-(4-((6-(3-((2,4-Dioxothiazolidin-5-ylidene)methyl)phenoxy)-5-methylpyrimidin-4-yl)oxy)piperidin-1-yl)nicotinonitrile;

(Z)-tert-Butyl-4-((6-(3-((3-benzyl-2,4-dioxothiazolidin-5-ylidene)methyl)phenoxy)-5-methylpyrimidin-4-yl)oxy)piperidine-1-carboxylate;

(Z)-tert-Butyl-4-((6-(3-((3-allyl-2,4-dioxothiazolidin-5-ylidene)methyl)phenoxy)-5-methylpyrimidin-4-yl)oxy)piperidine-1-carboxylate;

(Z)-tert-Butyl-4-((6-(3-((3-(2-bromoethyl)-2,4-dioxothiazolidin-5-ylidene)methyl)phenoxy)-5-methylpyrimidin-4-yl)oxy)piperidine-1-carboxylate;

(Z)-tert-Butyl-4-((6-(3-((3-ethyl-2,4-dioxothiazolidin-5-ylidene)methyl)phenoxy)-5-methylpyrimidin-4-yl)oxy)piperidine-1-carboxylate;

(Z)-3-Ethyl-5-(3-((6-((1-(5-ethylpyrimidin-2-yl)piperidin-4-yl)oxy)-5-methylpyrimidin-4-yl)oxy)benzylidene)thiazolidine-2,4-dione;

(Z)-5-(3-((6-((1-(5-Ethylpyrimidin-2-yl) piperidin-4-yl)oxy)-5-methylpyrimidin-4-yl)oxy)benzylidene)-3-(2-oxopropyl)thiazolidine-2,4-dione;

(Z)-5-(3-((6-((1-(isopropylsulfonyl)piperidin-4-yl)oxy)-5-methylpyrimidin-4-yl)oxy)benzylidene)thiazolidine-2,4-dione;

(Z)-5-(3-((6-((1-acetylpiperidin-4-yl)oxy)pyrimidin-4-yl)oxy)benzylidene)thiazolidine-2,4-dione;

(Z)-5-(4-((6-((1-acetylpiperidin-4-yl)oxy)pyrimidin-4-yl)oxy)benzylidene)thiazolidine-2,4-dione;

(Z)-5-(3-((6-((1-(3-isopropyl-1,2,4-oxadiazol-5-yl)piperidin-4-yl)oxy)pyrimidin-4-yl)oxy)benzylidene)thiazolidine-2,4-dione;

(Z)-5-(3-((6-((1-(3-isopropyl-1,2,4-oxadiazol-5-yl)piperidin-4-yl)oxy)-5-ethylpyrimidin-4-yl)oxy)benzylidene)-3-methylthiazolidine-2,4-dione;

(Z)-5-(3-((6-((1-(3-isopropyl-1,2,4-oxadiazol-5-yl)piperidin-4-yl)oxy)-5-ethylpyrimidin-4-yl)oxy)benzylidene)-3-(2-oxopropyl)thiazol dine-2,4-dione;

(Z)-3-isopropyl-5-(3-((6-((1-(3-isopropyl-1,2,4-oxadiazol-5-yl)piperidin-4-yl)oxy)-5-methylpyrimidin-4-yl)oxy)benzylidene)thiazolidine-2,4-dione;

(Z)-6-(4-((6-(3-((2,4-dioxothiazolidin-5-ylidene)methyl)phenoxy)pyrimidin-4-yl)oxy)piperidin-1-yl)nicotinonitrile;

(Z)-5-(3-((6-((1-(methyl sulfonyl)piperidin-4-yl)oxy)pyrimidin-4-yl)oxy)benzylidene)thiazolidine-2,4-dione;

(Z)-5-(3-((6-((1-(5-chloropyrimidin-2-yl)piperidin-4-yl)oxy)pyrimidin-4-yl)oxy)benzylidene)thiazolidine-2,4-dione;

(Z)-5-(4-((6-((1-(5-chloropyrimidin-2-yl)piperidin-4-yl)oxy)pyrimidin-4-yl)oxy)benzylidene)thiazolidine-2,4-dione;

(Z)-3-(methylsulfonyl)-5-(4-((6-((1-(methylsulfonyl)piperidin-4-yl)oxy)pyrimidin-4-yl)oxy)benzylidene)thiazolidine-2,4-dione;

(Z)-5-(4-((6-((1-(5-bromopyridin-2-yl)piperidin-4-yl)oxy)pyrimidin-4-yl)oxy)benzylidene)thiazolidine-2,4-dione; and (Z)-5-(3-((6-((1-(5-bromopyridin-2-yl)piperidin-4-yl)oxy)pyrimidin-4-yl)oxy)benzylidene)thiazolidine-2,4-dione.

7. A pharmaceutical composition comprising a compound of claim 1 and a pharmaceutically acceptable carrier, diluent or excipient.

8. A method for lowering glucose levels, comprising administering the compound of claim 1 to a mammal in need thereof.

9. A method for treating obesity, comprising administering the compound of claim 1 to a mammal in need thereof.

10. A method for treating diabetes comprising administering a compound of claim 1 to a mammal in need thereof.

11. A pharmaceutical composition of claim 7 wherein the compound of claim 1 is present in an effective amount to modulate a GPR-119 receptor.

12. A process for preparing a compound of claim 1 wherein $R_1$, $R_2$, $R_3$, X, A and n are as defined in claim comprising reacting a compound of formula (VI),

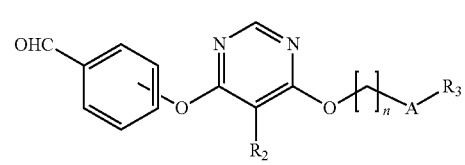

with a compound of formula (VII)

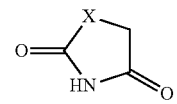

to obtain a compound of formula (Ia);

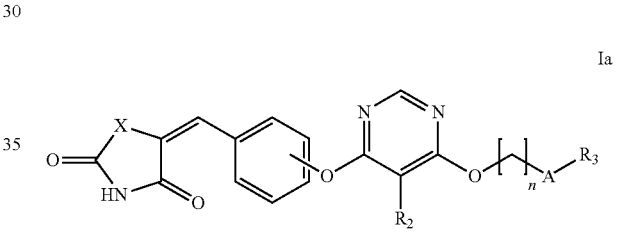

and reacting a compound of formula (Ia) with $R_1$-L, wherein L represents a suitable leaving group selected from a member of the group consisting of halogen, mesylate, tosylate, and triflate to yield a compound of formula (I)

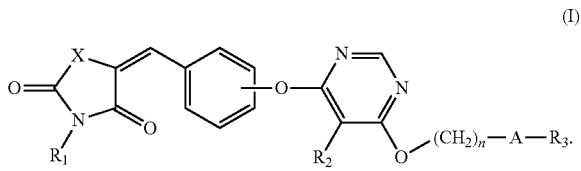

* * * * *